US012716896B2

(12) United States Patent
Allen et al.

(10) Patent No.: US 12,716,896 B2
(45) Date of Patent: Aug. 25, 2026

(54) ANTIBODY ASSAY FOR THE DETECTION AND TREATMENT OF LIVER CANCER

(71) Applicant: Freenome Holdings Inc., South San Francisco, CA (US)

(72) Inventors: Jared Allen, Nottingham (GB); Isabel Macdonald, Nottingham (GB); Andrea Murray, Nottingham (GB); Christopher Welberry, Nottingham (GB)

(73) Assignee: Freenome Holdings Inc., South San Francisco, CA (US)

( * ) Notice: Subject to any disclaimer, the term of this patent is extended or adjusted under 35 U.S.C. 154(b) by 328 days.

(21) Appl. No.: 16/463,549

(22) PCT Filed: Nov. 24, 2017

(86) PCT No.: PCT/GB2017/053541

§ 371 (c)(1),
(2) Date: May 23, 2019

(87) PCT Pub. No.: WO2018/096351

PCT Pub. Date: May 31, 2018

(65) Prior Publication Data

US 2019/0376975 A1 Dec. 12, 2019

(30) Foreign Application Priority Data

Nov. 25, 2016 (GB) ..................................... 1619954

(51) Int. Cl.
*G01N 33/57525* (2026.01)

(52) U.S. Cl.
CPC .............................. *G01N 33/57525* (2026.01)

(58) Field of Classification Search
CPC ........... G01N 33/57438; G01N 33/564; G01N 2800/52; G01N 33/57484; G01N 33/6893; G01N 2800/50
See application file for complete search history.

(56) References Cited

U.S. PATENT DOCUMENTS

| | | | | |
|---|---|---|---|---|
| 2008/0254481 | A1* | 10/2008 | Love | C12Y 207/10001 435/7.1 |
| 2013/0309234 | A1 | 11/2013 | Lindhofer | |
| 2017/0138951 | A1* | 5/2017 | Murray | G01N 33/57488 |

FOREIGN PATENT DOCUMENTS

| | | | |
|---|---|---|---|
| WO | WO 03/024304 | A2 | 3/2003 |
| WO | WO 2005/043165 | A2 | 5/2005 |
| WO | WO 2010/065944 | A1 | 6/2010 |
| WO | WO 2015/071669 | A2 | 5/2015 |
| WO | WO 2015/193678 | A1 | 12/2015 |

OTHER PUBLICATIONS

Zhang et al. Combined alpha fetoprotein testing and ultrasonography as a screening test for primary liver cancer. J. Med. Screen. 6: 108-110, 1999.*

Welberry et al. Tumor-associated autoantibodies in combination with alpha-fetoprotein for detection of early stage hepatocellular carcinoma. PLOS ONE, pp. 1-17, published May 6, 2020.*

Kai Breuhahn, Patrick A. Baeuerle, Maite Peters, Nadja Prang, Ulrich Töx, Rudolph Köhue-Volland, Volker Dries, Peter Schirnmacher, and Eugen Leo, "Expression of epithelial cellular adhesion molecule (Ep-CAM) in chronic (necro- ) inflammatory liver diseases and hepatocellular carcinoma," *Hepatology Research*, Jan. 2006, pp. 50-56.

Martin Heubner, Dino Errico, Sabine Kasimir-Bauer, Dorothee Herlyn, Rainer Kimmig, and Pauline Wimberger, "EpCAM-autoantibody levels in the course of disease of ovarian cancer patients," *Med. Oncol.*, Jun. 2011, 28: 626-630.

Carmelo Carmona-Rivera, Wenpu Zhao, Srilakshmi Yalavarthi, and Mariana J. Kaplan, "Neutrophil extracellular traps induce endothelial dysfunction in systemic lupus erythematosus through the activation of matrix metalloproteinase-2", *Ann. Rheum Dis.*, Feb. 25, 2014; 74: 1417-1424.

Oliver Schmetzer, Gerhard Moldenhauer, Rainer Riesenberg, José Ricardo Pires, Peter Schlag and Antonio Pezzutto, "Quality of Recombinant Protein Determines the Amount of Autoreactivity Detected against the Tumor-Associated Epithelial Cell Adhesion Molecule Antigen: Low Frequency of Antibodies against the Natural Protein," *J. Immunol.*, Jan. 15, 2005, 174: 942-952.

Oliver Schmetzer, Gerhard Moldenhauer, Annett Nicolaou, Peter Schlag, Rainer Riesenberg, and Antonio Pezzutto, "Detection of circulating tumor-associated antigen depends on the domains recognized by the monoclonal antibodies used: N-terminal trimmed EpCAM-levels are much higher than untrimmed forms," *Immunology Letters*, Feb. 22, 2012, 184-192.

(Continued)

*Primary Examiner* — Alana Harris Dent
(74) *Attorney, Agent, or Firm* — Finnegan, Henderson, Farabow, Garrett & Dunner LLP

(57) ABSTRACT

The present invention relates to a method of detecting liver cancer in a mammalian subject by detecting an antibody in a test sample comprising a bodily fluid from the mammalian subject, wherein the antibody is an autoantibody immunologically specific for a tumour marker protein selected from the group consisting of MMP9, AIF1, EpCAM and CDKN1B, which method comprises contacting the test sample with a tumour marker antigen selected from the group consisting of MMP9, AIF1, EpCAM and CDKN1B and determining the presence or absence of complexes of the tumour marker antigen bound to autoantibodies present in the test sample where the presence of said complexes is indicative of the presence of liver cancer. Also included within the invention are corresponding methods of diagnosing and treating liver cancer in a mammalian subject, corresponding methods of predicting response to an anti-liver cancer treatment, a corresponding method of detecting an antibody in a test sample comprising a bodily fluid from a mammalian subject and kits suitable for performing methods of the invention.

28 Claims, 4 Drawing Sheets

(56) References Cited

OTHER PUBLICATIONS

Muhammad, Wasif Saif et al., "The clinical significance of autoantibodies in gastrointestinal malignancies: an overview," Expert Opinin of Biological Therapy, vol. 7, No. 4, pp. 493-507 (2007).

Yoon, S.K., "Recent Advances in Tumor Markers of Human Hepatocellular Carcinoma," Intervirology, vol. 51 (Suppl 1), pp. 34-41 (2008).

International Search Report for International Application No. PCT/GB2017/053541, Apr. 4, 2018.

Written Opinion of the International Searching Authority for International Application No. PCT/GB2017/053541, Apr. 3, 2018.

* cited by examiner

|   | 1 | 2 | 3 | 4 | 5 | 6 | 7 | 8 | 9 | 10 | 11 | 12 |
|---|---|---|---|---|---|---|---|---|---|---|---|---|
|   | 160nm | 160nm | 160nm | 160nm | 160nm | 160nm | 50nM | 50nM | 50nM | 50nM | 50nM | 50nM |
| A | Blank | VOL | 1 | 2 | 3 | 4 | Blank | VOL | 1 | 2 | 3 | 4 |
| B | 5 | 6 | 7 | 8 | 9 | 10 | 5 | 6 | 7 | 8 | 9 | 10 |
| C | 11 | 12 | 13 | 14 | 15 | 16 | 11 | 12 | 13 | 14 | 15 | 16 |
| D | 17 | 18 | 19 | 20 | 21 | 22 | 17 | 18 | 19 | 20 | 21 | 22 |
| E | 23 | 24 | 25 | 26 | 27 | 28 | 23 | 24 | 25 | 26 | 27 | 28 |
| F | 29 | 30 | 31 | 32 | 33 | 34 | 29 | 30 | 31 | 32 | 33 | 34 |
| G | 35 | 36 | 37 | 38 | 39 | 40 | 35 | 36 | 37 | 38 | 39 | 40 |
| H | 41 | 42 | 43 | 44 | 45 | 46 | 41 | 42 | 43 | 44 | 45 | 46 |

Figure 2A

ANTIBODY ASSAY FOR THE DETECTION AND TREATMENT OF LIVER CANCER

This application is a national stage filing under 35 U.S.C. § 371 of International Application No. PCT/GB2017/053541, filed on Nov. 24, 2017, which claims priority of British Patent Application No. 1619954.9, filed Nov. 25, 2016. The contents of these applications are each incorporated herein by reference.

FIELD OF THE INVENTION

The invention relates generally to the field of antibody detection, and in particular relates to assays for the detection of autoantibodies relating to liver cancer in a sample comprising patient bodily fluid.

BACKGROUND OF THE INVENTION

Many diagnostic, prognostic and/or monitoring assays rely on detection of a biological marker of a particular disease state or disease susceptibility. Such biological markers are commonly proteins or polypeptides that are characteristic of a particular disease or associated with susceptibility to disease and are often used for the detection of cancers, including liver cancer.

Liver cancer, and specifically hepatocellular carcinoma (HCC), is the sixth most common cancer worldwide, yet it is the second most common cause of death from cancer. High mortality rates are caused by late diagnosis, often after metastasis, and pre-existing liver diseases. Late diagnosis is due to paucity of early symptoms and suboptimal imaging techniques for use in diagnosis.

Ultrasound screening and assessment of blood alpha-fetoprotein (AFP) levels are currently the widest used screening tools for liver cancer. However, their poor performance highlights a major gap for an improved early detection/screening test for liver cancer.

It is clear that a clinically useful test to effectively screen for the presence of liver cancer would be welcomed since it would allow liver cancer to be diagnosed early. Further, a diagnostic test performed on a sample of bodily fluid, e.g. a blood sample, would be quick and relatively non-invasive, increasing screening participation rates relative to other techniques. Early stage disease detection opens up a wider range of treatment options with less severe side effects. The current treatment pathways for moderate stage liver cancer involve a full liver transplant, and the earlier identification of patients with early stage disease will ease the load on the organ donor register.

An improved screening test for liver cancer would be useful around the world since rates of liver cancer are increasing worldwide. Currently, China accounts for around 50% of all HCC cases whilst Egypt also has a very high rate of HCC. The high prevalence of HCC in these countries is considered to be due, in part, to high incidence of hepatitis B in China and a high prevalence of hepatitis C in Egypt. Hepatitis B and hepatitis C are known risk factors for liver cancer along with liver cirrhosis, non-alcoholic fatty liver disease, alcoholic liver disease, Wilson's disease, hereditary hemochromatosis, autoimmune hepatitis, documented aflatoxin exposure, schistosomiasis and diabetes mellitus. The increasing prevalence of these conditions throughout the world makes it imperative that a quick and non-invasive test for liver cancer is devised.

In recent years it has become apparent that antibodies, and in particular autoantibodies, can serve as biological markers of disease or disease susceptibility. Autoantibodies are naturally occurring antibodies directed to an antigen which an individual's immune system recognises as foreign even though that antigen actually originated in the individual. They may be present in the circulation as circulating free autoantibodies or in the form of circulating immune complexes consisting of autoantibodies bound to their target protein. Differences between a wild type protein expressed by "normal" cells and an altered form of the protein produced by a diseased cell or during a disease process may, in some instances, lead to the altered protein being recognised by an individual's immune system as "non-self" and thus eliciting an immune response in that individual. This may be a humoral (i.e. B cell-mediated) immune response leading to the production of autoantibodies immunologically specific for the altered protein.

Assays which measure the immune response of an individual to the presence of tumour marker proteins in terms of autoantibody production provide an alternative to the direct measurement or detection of tumour marker proteins in bodily fluids. Such assays essentially constitute indirect detection of the presence of a tumour marker protein. The nature of the immune response means it is likely that autoantibodies can be elicited by a very small amount of circulating tumour marker protein and indirect methods which rely on detecting the immune response to tumour marker proteins will consequently be more sensitive than methods for the direct measurement of tumour marker protein levels in bodily fluids. Assay methods based on the detection of autoantibodies may therefore be of particular value early in the disease process.

The inventors have surprisingly determined four tumour marker antigens previously not known to be associated with liver cancer. Through the detection of autoantibodies directed to any one of these tumour marker antigens, optionally in combination with one or more additional tumour marker antigens, the inventors have devised an effective and non-invasive screening method for liver cancer, and a corresponding kit.

SUMMARY OF THE INVENTION

The inventors have surprisingly established that autoantibodies immunologically specific for any one of the tumour marker proteins matrix metallopeptidase 9 (MMP9), allograft inflammatory factor 1 (AIF1), epithelial cell adhesion molecule (EpCAM) and cyclin-dependent kinase inhibitor 1B (CDKN1B) are indicative of the presence of liver cancer. Therefore, the detection of autoantibodies immunologically specific for any one of these tumour marker proteins can be used for the diagnosis of liver cancer.

According to a first aspect of the invention there is provided a method of detecting an antibody in a test sample comprising a bodily fluid from a mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B; and (b) determining the presence or absence of complexes of the tumour marker antigen bound to autoantibodies present in the test sample.

Within this aspect the subject is preferably suspected of having liver cancer.

According to a second aspect of the invention there is provided a method of detecting liver cancer in a mammalian subject by detecting an antibody in a test sample comprising a bodily fluid from the mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B; and (b) determining the presence or absence of complexes of the tumour marker antigen bound to autoantibodies present in the test sample;

whereby the presence of said complexes is indicative of the presence of liver cancer.

According to a third aspect of the invention there is provided a method of diagnosing and treating liver cancer in a mammalian subject by detecting an antibody in a test sample comprising a bodily fluid from the mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B;

(b) determining the presence or absence of complexes of the tumour marker antigen bound to autoantibodies present in the test sample;

(c) diagnosing the subject with liver cancer when complexes of the tumour marker antigen bound to autoantibodies present in the test sample are detected; and (d) administering a liver cancer treatment to the diagnosed subject.

According to a fourth aspect of the invention there is provided a method of predicting response to an anti-liver cancer treatment, the method comprising detecting an antibody in a test sample comprising a bodily fluid from a mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B;

(b) determining the presence or absence of complexes of the tumour marker antigen bound to autoantibodies present in the test sample;

(c) detecting the amount of specific binding between the tumour marker antigen and autoantibodies present in the test sample; and (d) comparing the amount of specific binding between the tumour marker antigen and the autoantibody with a previously established relationship between the amount of binding and the likely outcome of treatment;

whereby a change in the amount of specific binding, when compared to controls, predicts that the patient will or will not respond to the anti-liver cancer treatment.

Within this aspect of the invention the anti-liver cancer treatment may be selected from the group consisting of chemotherapy, radiofrequency ablation, liver resection, liver transplant, vaccination, anti-growth factor or signal transduction therapies, endocrine therapy, human antibody therapy, transcatheter arterial chemoembolization, percutaneous ethanol injection, microwave ablation, sorafenib administration and radioembolization.

According to a fifth aspect of the invention there is provided use of a tumour marker antigen selected from the group consisting of MMP9, AIF1, EpCAM and CDKN1B in a method of detecting liver cancer in a mammalian subject by detecting an autoantibody immunologically specific for MMP9, AIF1, EpCAM or CDKN1B in a test sample comprising a bodily fluid from the mammalian subject, which method comprises the steps of:

(a) contacting the test sample with a tumour marker antigen selected from the group consisting of MMP9, AIF1, EpCAM and CDKN1B; and (b) determining the presence or absence of complexes of the tumour marker antigen bound to autoantibodies present in the test sample;

whereby the presence of said complexes is indicative of the presence of liver cancer.

According to a sixth aspect of the invention there is provided a kit for the detection of autoantibodies in a test sample comprising a bodily fluid from a mammalian subject comprising:

(a) a tumour marker antigen selected from the group consisting of MMP9, AIF1, EpCAM and CDKN1B; and (b) a reagent capable of detecting complexes of the tumour marker antigen bound to autoantibodies present in the test sample.

According to a seventh aspect of the invention there is provided an in vitro method of determining an antibody profile of an individual suffering from liver cancer in a test sample comprising a bodily fluid from the mammalian subject wherein the antibody is an autoantibody immunologically specific for a tumour marker protein selected from the group consisting of MMP9, AIF1, EpCAM and CDKN1B, which method comprises the steps of:

a) contacting the test sample with a tumour marker antigen selected from the group consisting of MMP9, AIF1, EpCAM and CDKN1B; and b) determining the presence or absence of complexes of the tumour marker antigen bound to autoantibodies present in the test sample, wherein the method is repeated to build up a profile of antibody production.

In all aspects of the invention the mammalian subject is preferably a human. Herein the terms "mammalian subject" and "subject" will be used interchangeably to refer to a subject who is mammalian, preferably human.

In all aspects of the invention the method is preferably carried out in vitro on a test sample comprising a bodily fluid obtained or prepared from the mammalian subject.

The surprising discovery that autoantibodies immunologically specific for a tumour marker protein selected from the group consisting of MMP9, AIF1, EpCAM and CDKN1B can be used as markers for liver cancer has permitted the inventors to devise methods for the detection of such autoantibodies, which can be used to detect and diagnose liver cancer. Such detection can be performed using a kit, and these methods and kits form the core of the present invention.

BRIEF DESCRIPTION OF FIGURES

FIG. 1. Diagrammatic representation to demonstrate the derivation of secondary curve parameters.

FIG. 2. Autoantibody microtitre plate layouts: FIG. 2A=high-throughput assay (HTPA) layout.

DETAILED DESCRIPTION OF THE INVENTION

Figure 1A:
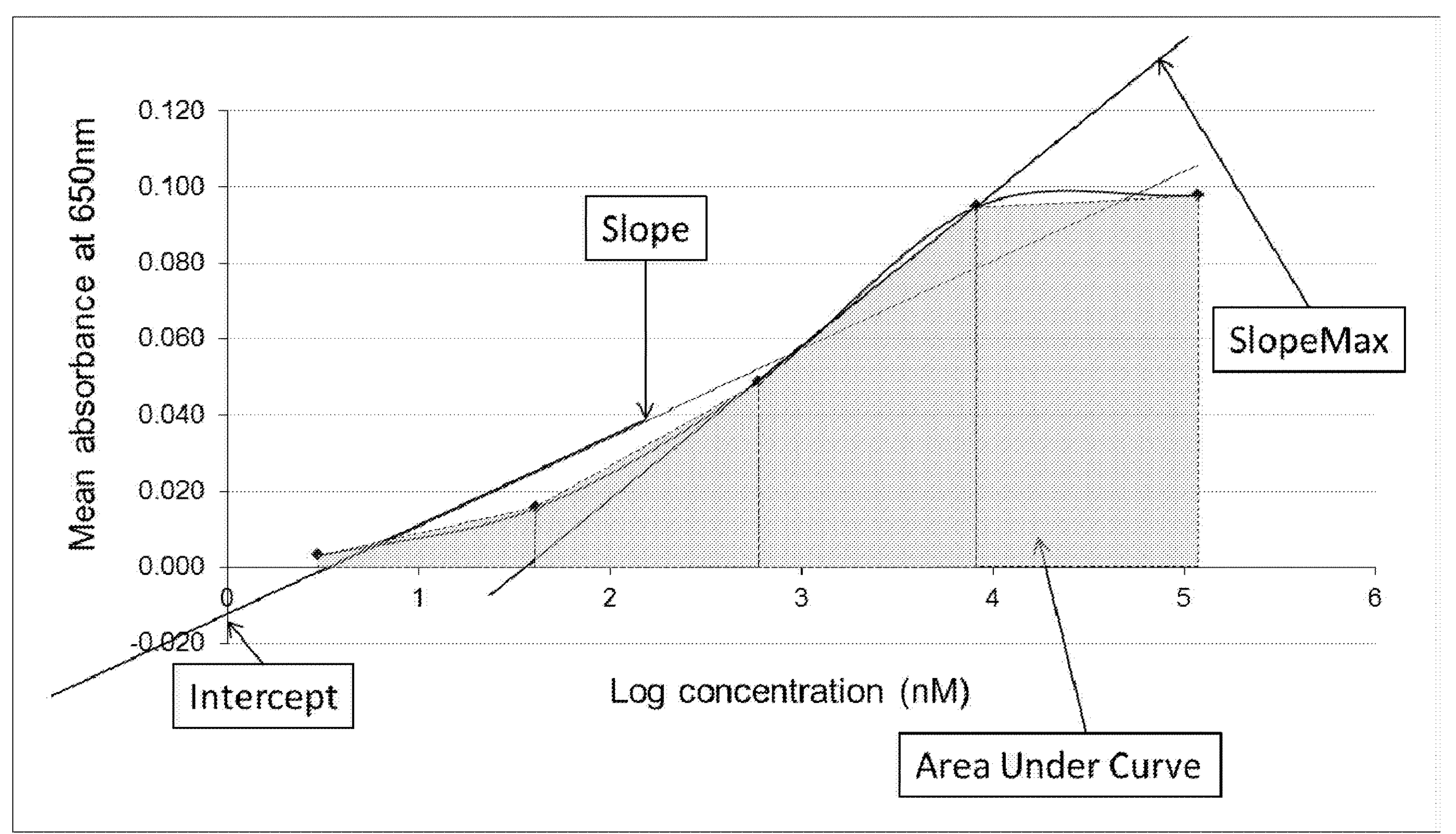
FIG. 1A=Slope, Intercept, Area under the Curve (AUC) and SlopeMax.

The invention provides, in general, an immunoassay method for detecting an autoantibody immunologically specific for a tumour marker protein selected from the group consisting of MMP9, AIF1, EpCAM and CDKN1B. This immunoassay method may be used to detect or diagnose liver cancer.

Method of Detecting an Autoantibody

According to a first aspect of the invention there is provided a method of detecting an antibody in a test sample comprising a bodily fluid from a mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B; and
(b) determining the presence or absence of complexes of the tumour marker antigen bound to autoantibodies present in the test sample.

The term "autoantibody" used herein refers to a naturally occurring antibody directed to an antigen which an individual's immune system recognises as foreign even though that antigen actually originated in the individual. In general, autoantibodies include antibodies directed against altered forms of naturally occurring proteins produced by a diseased cell or during a disease process. The altered form of the protein originates in the individual but may be viewed by the individual's immune system as "non-self" and thus elicit an immune response in that individual in the form of autoantibodies immunologically specific to the altered protein. Such altered forms of a protein can include, for example, mutants having altered amino acid sequence, optionally accompanied by changes in secondary, tertiary or quaternary structure, truncated forms, splice variants, altered glycoforms etc. In other embodiments the autoantibody may be directed to a protein which is overexpressed in a disease state, or as a result of gene amplification or abnormal transcriptional regulation. Overexpression of a protein which is not normally encountered by cells of the immune system in significant amounts can trigger an immune response leading to autoantibody production. In further embodiments the autoantibody may be directed to a foetal form of a protein which becomes expressed in a disease state. If a foetal protein which is normally expressed only in early stages of development, before the immune system is functional, becomes expressed in a disease state, the foetal form expressed in a disease state in the fully developed human may be recognised by the immune system as "foreign", triggering an immune response leading to autoantibody production. In still further embodiments the autoantibody may be directed against a protein which is expressed at a different location in a disease state. For example, the protein may be expressed at an internal location in healthy individuals but is expressed at a surface exposed location in a disease state such that it is exposed to the circulation and therefore the immune system in the disease state but not in the healthy individual. Herein the protein to which the autoantibody is directed will be referred to as a "tumour marker protein".

Within the scope of the invention it is contemplated that autoantibodies immunologically specific for any one of MMP9, AIF1, EpCAM and CDKN1B may be detected. The invention also contemplates the detection of autoantibodies which are immunologically specific for one of these tumour marker proteins and autoantibodies which are immunologically specific for a second of these tumour marker proteins, optionally in combination with detection of autoantibodies which are immunologically specific for a third of these tumour marker proteins and further optionally detection of autoantibodies which are immunologically specific the fourth of these tumour marker proteins. However, the invention is in no way limited in this regard. Where autoantibodies immunologically specific for two or three of the identified tumour marker proteins are detected, all combinations of two or three tumour marker proteins are contemplated.

In the context of the present invention the term "antigen" is used to refer to an immunospecific reagent which complexes with autoantibodies present in the test sample. An antigen is a substance comprising at least one antigenic determinant or epitope capable of interacting specifically with the target autoantibody it is desired to detect, or any capture agent interacting specifically with the variable region or complementary determining regions of said autoantibody. The antigen will typically be a naturally occurring or synthetic biological macromolecule such as, for example, a protein or peptide, a polysaccharide or a nucleic acid and can include antibodies or fragments thereof such as anti-idiotype antibodies. A "tumour marker antigen" is an antigen elevated in subjects with cancer, specifically in this context liver cancer. Herein the terms "tumour marker antigen" and "antigen" will be used interchangeably.

As used herein the term "bodily fluid", when referring to the material to be tested for the presence of autoantibodies using the method of the invention, includes inter alia plasma, serum, whole blood, urine, sweat, lymph, faeces, cerebrospinal fluid, ascites fluid, pleural effusion, seminal fluid, sputum, nipple aspirate, post-operative seroma, saliva, amniotic fluid, tears or wound drainage fluid. As aforesaid, the methods of the invention are preferably carried out in vitro on a test sample comprising bodily fluid removed from the test subject. The type of bodily fluid used may vary depending upon the identity of the autoantibody to be tested and the clinical situation in which the assay is used. In general, it is preferred to perform the assays on samples of serum or plasma. The test sample may include further components in addition to the bodily fluid such as for example diluents, preservatives, stabilising agents, buffers etc.

In certain embodiments, the method of the invention may further comprise the step of:

(c) detecting the amount of specific binding between the tumour marker antigen and autoantibodies present in the test sample, wherein the presence or absence of the autoantibody is based upon a comparison between the amount of specific binding observed and a pre-determined cut-off.

Within this embodiment the amount of specific binding between the tumour marker antigen and autoantibodies present in the test sample may be the relative amount of binding or the absolute amount of binding.

Here, the autoantibody may be considered to be present if the amount of specific binding between the tumour marker antigen and autoantibodies present in the test sample is either above or below a pre-determined cut-off. However, generally the autoantibody is considered to be present if the amount of specific binding between the tumour marker antigen and autoantibodies present in the test sample is above a pre-determined cut-off. The pre-determined cut-off may be determined by performing a control assay on known negative samples (e.g. normal individuals) in case-controlled studies. The "normal" individuals will preferably be age-matched controls not having any diagnosis of liver cancer based on clinical, imaging and/or biochemical criteria. In certain embodiments the known negative samples may be derived from individuals with benign liver disease, i.e. those individuals which are at high risk of liver cancer but have not shown any evidence of liver cancer. Preferably the normal individuals do not have any diagnosis of any cancer. Here the amount of specific binding between the tumour marker antigen and autoantibodies present in test samples from normal patients may be detected and averaged to provide a pre-determined cut-off. In certain embodiments the pre-determined cut-off may be determined by selecting the cut-off value giving the largest Youden's value which keeps specificity greater than 90%.

The inventors have surprisingly discovered that autoantibodies immunologically specific for any one of MMP9, AIF1, EpCAM and CDKN1B are associated with liver cancer. Therefore, in certain embodiments, the subject may be suspected of having liver cancer. Any reason for suspecting that a subject may have liver cancer is contemplated.

Within all aspects of the present invention, the liver cancer may be hepatocellular carcinoma (HCC).

In certain embodiments the mammalian subject may be suspected of having liver cancer because they have previously tested positive in a liver cancer screen. Here any liver cancer screen is contemplated. In certain embodiments the subject may have previously tested positive for alpha-fetoprotein (AFP). Generally, AFP levels are detected in a blood sample taken from the subject and the subject may therefore have previously tested positive for AFP in a blood sample. However, any AFP detection technique is contemplated. In alternative embodiments, the subject may have previously tested positive for des-gamma carboxyprothrombin (DCP) or lectin-reactive alpha-fetoprotein (AFP-L3). Generally, DCP and AFP-L3 levels are detected in a blood sample taken from the subject and the subject may therefore have previously tested positive for DCP or AFP-L3 in a blood sample. However, any DCP or AFP-L3 detection technique is contemplated.

In other embodiments the subject may have tested positive for liver cancer using ultrasound surveillance or any other imaging method.

Within the bounds of the present invention the subject may have tested positive in a liver cancer screen at any point prior to performance of the method of the invention. For example, the liver cancer screen may have been performed one hour, two hours, three hours, four hours, five hours, six hours, seven hours, eight hours, nine hours, ten hours, eleven hours, twelve hours, twenty four hours, two days, three days, four days, five days, six days, one week, two weeks, three weeks, four weeks, one month, two months, three months, four months, five months, six months, one year, two years, three years, four years, five years, six years, seven years, eight years, nine years, ten years or more before performance of the method of the invention.

For the purposes of the invention, subjects which are undergoing treatment for liver cancer or which have previously undergone treatment for liver cancer may still be considered "suspected of having liver cancer". Herein the treatment for liver cancer may have been performed at any time and the subject may or may not have subsequently been tested for the presence of liver cancer.

The subject may be suspected of having liver cancer due to the presence of a known risk factor for liver cancer. In certain embodiments the subject may have liver cirrhosis, non-alcoholic fatty liver disease, alcoholic liver disease, Wilson's disease, hereditary hemochromatosis, autoimmune hepatitis, hepatitis B, hepatitis C, documented aflatoxin exposure, schistosomiasis or diabetes mellitus. Any methods of determining these risk factors are contemplated and the subject may or may not be undergoing or have undergone treatment relevant to the risk factor.

Since the inventors have surprisingly determined that autoantibodies immunologically specific for MMP9, AIF1, EpCAM and CDKN1B are associated with liver cancer, the detection in a test sample of autoantibodies immunologically specific for any one of these tumour marker proteins can be used in a method of detecting liver cancer. In one aspect the invention therefore provides a method of detecting liver cancer in a mammalian subject by detecting an antibody in a test sample comprising a bodily fluid from the mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B; and
(b) determining the presence or absence of complexes of the tumour marker antigen bound to autoantibodies present in the test sample;
whereby the presence of said complexes is indicative of the presence of liver cancer.

In its broadest aspects, the present invention relates to methods for detecting autoantibodies immunologically specific for any one of MMP9, AIF1, EpCAM and CDKN1B, and is not limited to the diagnosis of liver cancer or any subsequent treatment. However, in one aspect the invention provides a method of diagnosing and treating liver cancer in a mammalian subject by detecting an antibody in a test sample comprising a bodily fluid from the mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B;
(b) determining the presence or absence of complexes of the tumour marker antigen bound to autoantibodies present in the test sample;
(c) diagnosing the subject with liver cancer when complexes of the tumour marker antigen bound to autoantibodies present in the test sample are detected; and
(d) administering a liver cancer treatment to the diagnosed subject.

Within this aspect, the autoantibody may be considered to be present if the amount of specific binding between the tumour marker antigen and autoantibodies present in the test sample is either above or below a pre-determined cut-off, as explained above.

Within the bounds of the invention, the liver cancer treatment may be administered at any time following the diagnosis of liver cancer. For example, the liver cancer treatment may be administered one hour, two hours, three hours, four hours, five hours, six hours, seven hours, eight hours, nine hours, ten hours, eleven hours, twelve hours, twenty four hours, two days, three days, four days, five days, six days, one week, two weeks, three weeks, four weeks, one month, two months, three months, four months, five months, six months, one year or more after the diagnosis of liver cancer. Multiple administrations of liver cancer treatment with any spacing between rounds of treatment are also contemplated.

Administration of the liver cancer treatment at a geographical location different from the geographical location at which the liver cancer diagnosis was performed is contemplated. Further, the liver cancer treatment may be administered by a person different from the person performing the diagnosis, irrespective of whether the diagnosis and treatment are performed at the same or different geographical locations.

In one aspect, the autoantibody detection method of the invention may be used for treatment stratification, i.e. to determine whether a particular patient or group of patients is more or less likely to respond to a particular anti-liver cancer treatment. For example, the autoantibody detection method of the invention may be used to predict a subject's response to an anti-liver cancer treatment.

The invention therefore provides a method of predicting response to an anti-liver cancer treatment, the method comprising detecting an antibody in a test sample comprising a bodily fluid from a mammalian subject, wherein the antibody is an autoantibody immunologically specific for a tumour marker protein selected from the group consisting of MMP9, AIF1, EpCAM and CDKN1B, which method comprises the steps of:

(a) contacting the test sample with a tumour marker antigen selected from the group consisting of MMP9, AIF1, EpCAM and CDKN1B;

(b) determining the presence or absence of complexes of the tumour marker antigen bound to autoantibodies present in the test sample;

(c) detecting the amount of specific binding between the tumour marker antigen and autoantibodies present in the test sample; and (d) comparing the amount of specific binding between the tumour marker antigen and the autoantibody with a previously established relationship between the amount of binding and the likely outcome of treatment;

whereby a change in the amount of specific binding, when compared to controls, predicts that the patient will or will not respond to the anti-liver cancer treatment.

Herein, the control is preferably a sample of bodily fluid derived from a subject known to have liver cancer and known not to respond to the anti-liver cancer treatment being tested, i.e. to be a non-responding control.

It should be noted that the invention is in no way limited to any specific liver cancer treatment. In certain embodiments the liver cancer treatment may be selected from the group consisting of chemotherapy, radiofrequency ablation, liver resection, liver transplant, vaccination, anti-growth factor or signal transduction therapies, endocrine therapy, human antibody therapy, transcatheter arterial chemoembolization, percutaneous ethanol injection, microwave ablation, sorafenib administration and radioembolisation.

The aspects of the invention described above will usually be performed once. However, in vitro immunoassays are non-invasive and can be repeated as often as is thought necessary to build up a profile of autoantibody production in a patient, either prior to the onset of liver cancer, as in the screening of "at risk" individuals, or throughout the course of the disease.

The invention therefore provides an in vitro method of determining an antibody profile of an individual suffering from liver cancer in a test sample comprising a bodily fluid from the mammalian subject wherein the antibody is an autoantibody immunologically specific for a tumour marker protein selected from the group consisting of MMP9, AIF1, EpCAM and CDKN1B, which method comprises the steps of:

a) contacting the test sample with a tumour marker antigen selected from the group consisting of MMP9, AIF1, EpCAM and CDKN1B; and b) determining the presence or absence of complexes of the tumour marker antigen bound to autoantibodies present in the test sample, wherein the method is repeated to build up a profile of antibody production.

Panels of Two or More Tumour Marker Antigens

In certain embodiments of the invention the methods may detect two or more autoantibodies. For example, the methods may detect two, three, four, five, six, seven, eight, nine, ten, eleven, twelve, thirteen, fourteen, fifteen, sixteen, seventeen, eighteen, nineteen, twenty, twenty one, twenty two, twenty three, twenty four, twenty five, twenty six, twenty seven, twenty eight, twenty nine, thirty, thirty one, thirty two, thirty three, thirty four, thirty five, thirty six, thirty seven, thirty eight or more autoantibodies. In accordance with the core of the invention, one of the autoantibodies is immunologically specific for a tumour marker protein selected from the group consisting of MMP9, AIF1, EpCAM and CDKN1B.

Within these Embodiments the Method Comprises the Step of:

(a) contacting the test sample with a panel of two or more tumour marker antigens comprising a tumour marker antigen selected from the group consisting of MMP9, AIF1, EpCAM and CDKN1B and one or more further tumour marker antigens immunologically specific for at least one of said autoantibodies.

These methods may be hereinafter referred to as "panel assays". Such assays are generally more sensitive than the detection of autoantibodies to a single tumour marker antigen and give a much lower frequency of false negative results (see WO 99/58978, WO 2004/044590 and WO2006/126008, the contents of which are incorporated herein by reference).

It is generally accepted that the sensitivity of an assay will be increased by testing for the presence of multiple autoantibodies. Therefore, in some embodiments the methods of the invention contemplate the use of a panel comprising multiple tumour marker antigens, such as two, three, four, five, six, seven, eight, nine, ten, eleven, twelve, thirteen, fourteen, fifteen, sixteen, seventeen, eighteen, nineteen, twenty, twenty one, twenty two, twenty three, twenty four, twenty five, twenty six, twenty seven, twenty eight, twenty nine, thirty, thirty one, thirty two, thirty three, thirty four, thirty five, thirty six, thirty seven, thirty eight or more tumour marker antigens.

It should be noted that the panel embodiment may be used with all methods of the invention, including methods of detecting an autoantibody, methods of detecting liver cancer, methods of diagnosing and treating liver cancer, methods of predicting response to an anti-liver cancer treatment and methods of determining an antibody profile.

In certain embodiments the panel may comprise two or more tumour marker antigens which are distinct antigens. Herein, the term "distinct antigens" encompasses antigens derived from different proteins or polypeptides (such as antigens derived from unrelated proteins encoded by different genes).

The invention also contemplates methods utilising a panel which comprises two or more antigen variants of one or more of the distinct antigens. The term, "antigen variant" is used herein to refer to allelic or other variants of a single antigen, such as a single protein antigen as defined above. Antigen variants will generally be derived from a single gene, and different antigen variants may be expressed in different members of the population or in different disease states. Antigen variants may differ by amino acid sequence or by a post translational modification such as glycosylation, phosphorylation or acetylation. In addition, the term "antigen variant" encompasses antigen mutations such as amino acid substitutions, additions or deletions. Generally an antigen variant will contain less than five (e.g. less than four, less than three, less than two or one) mutations relative to the wild-type antigen.

Within the panel embodiment, the "one or more further tumour marker antigens" is preferably immunologically specific for an autoantibody other than the autoantibody immunologically specific for a tumour marker protein selected from the group consisting of MMP9, AIF1, EpCAM and CDKN1B, as discussed further below. However, although the invention is in no way limited in this regard, the invention does contemplate the detection of autoantibodies which are immunologically specific for one of these four tumour marker proteins and autoantibodies which are immunologically specific for a second of these four tumour marker proteins, optionally in combination with detection of autoantibodies which are immunologically specific for a third of these four tumour marker proteins and further optionally in combination with detection of autoantibodies which are immunologically specific for the fourth of these four tumour marker proteins. Where autoantibodies immunologically specific for two or three of the identified tumour marker proteins are detected, all combinations of two or three tumour marker proteins are contemplated. The panel of two or more tumour marker antigens may therefore comprise two, three or four tumour marker antigens selected from the group consisting of MMP9, AIF1, EpCAM and CDKN1B. In a certain specific embodiment, the panel may comprise MMP9, AIF1, EpCAM and CDKN1B. In a further specific embodiment, the panel may consist of MMP9, AIF1, EpCAM and CDKN1B.

In one embodiment, the panel of two or more tumour marker antigens may comprise one or more tumour marker antigens selected from the group consisting of NY-ESO-1, vimentin, HSPA4, transferrin, HNRNP-L, HSPD1, HNRNP-A2, SALL4, NPM1, YWHAZ, DDX3X, p62, CAGE, MAGE A4, RalA, GBU4-5, Cyclin B1, AFP, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1. Within this embodiment the panel may comprise one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four, twenty five, twenty six, twenty seven, twenty eight, twenty nine, thirty, thirty one, thirty two, thirty three or thirty four of the recited tumour marker antigens. In accordance with the invention, the panel will also comprise MMP9, AIF1, EpCAM or CDKN1B and may comprise one, two, three or four of these tumour marker antigens. In embodiments where two or three of these tumour marker antigens are included in the panel, all combinations of two or three of these antigens are contemplated. In specific embodiments the panel may comprise MMP9, AIF1, EpCAM and CDKN1B.

In one embodiment, the panel of two or more tumour marker antigens may comprise MMP9, AIF1, EpCAM, NY-ESO-1, HSPA4, vimentin, HNRNP-L and transferrin. In another embodiment the panel of two or more tumour marker antigens may consist of MMP9, AIF1, EpCAM, NY-ESO-1, HSPA4, vimentin, HNRNP-L and transferrin.

In another embodiment, the panel of two or more tumour marker antigens may comprise AIF1, EpCAM, HSPA4 and CPS1. In another embodiment the panel of two or more tumour marker antigens may consist of AIF1, EpCAM, HSPA4 and CPS1.

In a further embodiment, the panel of two or more tumour marker antigens may comprise EpCAM, NY-ESO-1, vimentin, HSPA2, HSPA4 and HNRNP-L. In another embodiment the panel of two or more tumour marker antigens may consist of EpCAM, NY-ESO-1, vimentin, HSPA2, HSPA4 and HNRNP-L.

In a still further embodiment, the panel of two or more tumour marker antigens may comprise MMP9, AIF1, EpCAM, DDX3X, SALL4, MAGE A4, NY-ESO-1, CAGE, RalA and SOX2. In another embodiment the panel of two or more tumour marker antigens may consist of MMP9, AIF1, EpCAM, DDX3X, SALL4, MAGE A4, NY-ESO-1, CAGE, RalA and SOX2.

In a still further embodiment, the panel of two or more tumour marker antigens may comprise EpCAM, CAGE, SOX2, RalA, MAGE A4, DDX3X and NY-ESO-1. In another embodiment the panel of two or more tumour marker antigens may consist of EpCAM, CAGE, SOX2, RalA, MAGE A4, DDX3X and NY-ESO-1.

In a still further embodiment, the panel of two or more tumour marker antigens may comprise AIF1, CAGE, HSPD1, SOX2, SALL4, HSPA4 and transferrin. In another embodiment the panel of two or more tumour marker antigens may consist of AIF1, CAGE, HSPD1, SOX2, SALL4, HSPA4 and transferrin.

In certain specific embodiments, the panel of two or more tumour marker antigens may differ depending upon the gender of the subject, i.e. whether the subject is male or female. Within this embodiment the panel of two or more tumour marker antigens may comprise or consist of AIF1, EpCAM, HSPA4 and CPS1, or AIF1, CAGE, HSPD1, SOX2, SALL4, HSPA4 and transferrin when the subject is female. Further within this embodiment, the panel of two or more tumour marker antigens may comprise or consist of EpCAM, NY-ESO-1, vimentin, HSPA2, HSPA4 and HNRNP-L, or EpCAM, CAGE, SOX2, RalA, MAGE A4, DDX3X and NY-ESO-1 when the subject is male.

In a specific embodiment, the panel of two or more tumour marker antigens may comprise NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1. In accordance with the invention, the panel will also comprise MMP9, AIF1, EpCAM or CDKN1B, and may comprise one, two, three or four of these tumour marker antigens. In embodiments where two or three of these tumour marker antigens are included in the panel, all combinations of two or three of these antigens are contemplated.

In specific embodiments the panel may comprise MMP9, AIF1, EpCAM and CDKN1B. For example, the panel of two or more tumour marker antigens may comprise MMP9, AIF1, EpCAM, CDKN1B, NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1.

In a specific embodiment the panel of two or more tumour marker antigens may consist of MMP9, AIF1, EpCAM, CDKN1B, NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1.

In a specific embodiment the panel of two or more tumour marker antigens may comprise CAGE, NY-ESO-1, MMP9, transferrin, MAGE A4, RalA, HSPA4, SALL4, Cyclin B1, EpCAM, DDX3X, and AIF1. In another embodiment the panel of two or more tumour marker antigens may consist of CAGE, NY-ESO-1, MMP9, transferrin, MAGE A4, RalA, HSPA4, SALL4, Cyclin B1, EpCAM, DDX3X, and AIF1.

In a specific embodiment the panel of two or more tumour marker antigens may comprise CAGE, NY-ESO-1, MMP9, transferrin, MAGE A4, RalA, HSPA4, SALL4, Cyclin B1, EpCAM, DDX3X, AIF1, SOX2 and AFP. In another embodiment the panel of two or more tumour marker antigens may consist of CAGE, NY-ESO-1, MMP9, transferrin, MAGE A4, RalA, HSPA4, SALL4, Cyclin B1, EpCAM, DDX3X, AIF1 SOX2 and AFP.

Additional Screening Steps

In certain embodiments of the present invention, the methods of the invention may further comprise screening for an additional marker associated with liver cancer. Within this embodiment any method of screening for any marker known to be associated with liver cancer is contemplated.

For example, the method may further comprise detecting alpha-fetoprotein (AFP), des-gamma carboxyprothrombin (DCP) or lectin-reactive alpha-fetoprotein (AFP-L3) in a test sample comprising a bodily fluid from the mammalian subject. Preferably the bodily fluid is blood. In embodiments in which the method further comprises detecting alpha-fetoprotein (AFP) in a test sample comprising a bodily fluid from the mammalian subject, the bodily fluid is preferably blood and a cut-off of 200 ng/ml is preferably applied to assess positivity.

Antigen Titration

In WO2006/126008 (the contents of which are incorporated herein by reference), it was determined that the performance, and more specifically the clinical utility and reliability, of assays based on the detection of autoantibodies as biological markers of disease can be improved dramatically by the inclusion of an antigen titration step. By testing the sample suspected of containing autoantibodies against a series of different amounts of antigen and constructing a titration curve it is possible to reliably identify true positive screening results independently of the absolute amount of autoantibody present in the sample. The antigen titration method of WO2006/126008 provides greater specificity and sensitivity than measuring autoantibody reactivity at a single antigen concentration, or methods in which the serum sample is titrated rather than the antigen.

In certain embodiments, the invention therefore contemplates methods wherein the tumour marker antigen is provided in a plurality of different amounts, and wherein the method comprises the steps of:

(a) contacting the test sample with a plurality of different amounts of the tumour marker antigen;
(b) determining the presence or absence of complexes of the tumour marker antigen bound to autoantibodies present in the test sample;
(c) detecting the amount of specific binding between the tumour marker antigen and the autoantibodies;
(d) plotting or calculating a curve of the amount of the specific binding versus the amount of tumour marker antigen for each amount of tumour marker antigen used in step (a); and
(e) determining the presence or absence of the autoantibody based upon the amount of specific binding between the tumour marker antigen and the autoantibody at each different amount of tumour marker antigen used.

In practice the different amounts of the tumour marker antigen will generally be provided by altering the concentration of the tumour marker antigen utilised. Therefore, the terms "different amount" and "different concentration" may be used interchangeably. However, within the scope of the invention, any method of altering the amount of tumour marker antigen is contemplated. Skilled readers will appreciate that in the method of the invention the amount of antigenic determinants or epitopes available for binding to the target autoantibody is important for establishing a titration series (i.e. a set of antigens provided in different amounts). In many assay formats the amount of antigenic determinants or epitopes available for binding is directly correlated with the amount of antigen molecules present. However, in other embodiments, such as certain solid phase assay systems, the amount of exposed antigenic determinants or epitopes may not correlate directly with the amount of antigen but may depend on other factors, such as attachment to the solid surface and conformational presentation. In these embodiments, references herein to "different amounts of antigen" in a titration series may be taken to refer to different amounts of the antigenic determinant or epitope. In particular embodiments, variation in the amount of antigen may be achieved by changing the antigen or epitope density against which the sample is tested, or by maintaining antigen or epitope density but increasing the surface area over which antigen is immobilised, or both.

Within this embodiment, a "set of antigens" refers to a single antigen to be tested at different amounts in the method of the invention.

In embodiments where multiple antigens are contemplated, a "set of distinct antigens" refers to a single antigen to be tested at different amounts in the method of the invention, wherein each antigen is a "distinct antigen" derived from different proteins or polypeptides (such as antigens derived from unrelated proteins encoded by different genes), as defined above. A given microarray may include exclusively sets of distinct antigens derived from different proteins or polypeptides, or exclusively sets of distinct antigens derived from different peptide epitopes of a single protein or polypeptide, or a mixture of the two in any proportion. It should be noted that each individual set of antigens of different amounts in any embodiment of the invention will generally comprise just one antigen and not mixtures thereof.

A set of antigen variants refers to a single antigen variant to be tested at different amounts in the method of the invention.

In certain embodiments, the presence or absence of the autoantibody may be determined based upon the collective values of the amount of specific binding for all of the amounts of tumour marker antigen used. During the methods of the invention the relative or absolute amount of specific binding between autoantibody and the antigen is determined for each different amount of antigen (antigenic determinant or epitope) tested and used to plot or calculate a curve of the (relative or absolute) amount of specific binding versus the amount of antigen for each amount of antigen tested. The presence in the test sample of autoantibody reactive with the antigen used in the assay is determined based upon the amount of specific binding observed at each antigen amount and is generally indicated by a dose-response curve, which is typically S-shaped or sigmoidal. Therefore, in certain embodiments the presence or absence of the autoantibody is determined by screening the plot for the presence of a dose response curve such as a generally S-shaped or sigmoidal curve. If there is no variation in detectable binding over the different amounts of antigen tested then this can be scored as an absence of a detectable amount of the autoantibody.

In one embodiment, the presence or absence of autoantibody is determined by comparison of the amount of specific binding between the autoantibody and the antigen with pre-determined cut-off values. Here, a curve of the amount of specific binding versus the amount of antigen for each amount of antigen used in the titration series is plotted, and the level of binding in known positive samples (e.g. a populations of patients with disease) are compared with the level of binding observed in known negative samples (e.g. normal individuals) in case-controlled studies. Cut-off values for autoantibody binding at one or more points on the titration curve are chosen that maximise sensitivity (few false negatives) while maintaining high specificity (few false positives). Provided the curve of the amount of specific binding versus the amount of antigen for each amount of antigen used in the titration series is a dose response curve, a measurement is considered to be positive if the amount of specific binding determined for one or more points on the titration curve is above the predetermined cut-off point value. In certain embodiments the pre-determined cut-off may be determined by selecting the cut-off value giving the largest Youden's value whilst keeping specificity greater than 90%.

It should be noted that the antigen titration embodiment may be used with all methods of the invention, including methods of detecting an autoantibody, methods of detecting liver cancer, methods of diagnosing and treating liver cancer, methods of predicting response to an anti-liver cancer treatment and methods of determining an antibody profile. In addition, antigen titration may be used in embodiments wherein only a single autoantibody is detected as well as in embodiments where a panel of antigens is used to detect multiple autoantibodies.

Double Cut-Off

It is generally accepted that the sensitivity of an assay will be increased by measuring autoantibodies against multiple antigens. However, this increased sensitivity is usually associated with a proportional decrease in specificity and assay methods may therefore be limited in the number of antigens which they can use. In certain embodiments the present method may account for the decrease in specificity by using an antigen titration method which determines the level of specific binding between the autoantibody and the antigen and assessment of a secondary curve parameter, with only test results considered positive when compared to cut-off points for both of these metrics being classified as positive. This method will be referred to herein as the "double cut-off" method and is fully described in WO2015/193678 (the contents of which are incorporated herein by reference).

In Certain Embodiments the Methods of the Invention Further Comprise the Steps of:

(d1) calculating a secondary curve parameter from the curve plotted or calculated in step (c); and (e) determining the presence or absence of the autoantibody based upon a combination of:

(i) the amount of specific binding between the autoantibody and the tumour marker antigen determined in step (b); and (ii) the secondary curve parameter determined in step (d1).

Figure 1B:
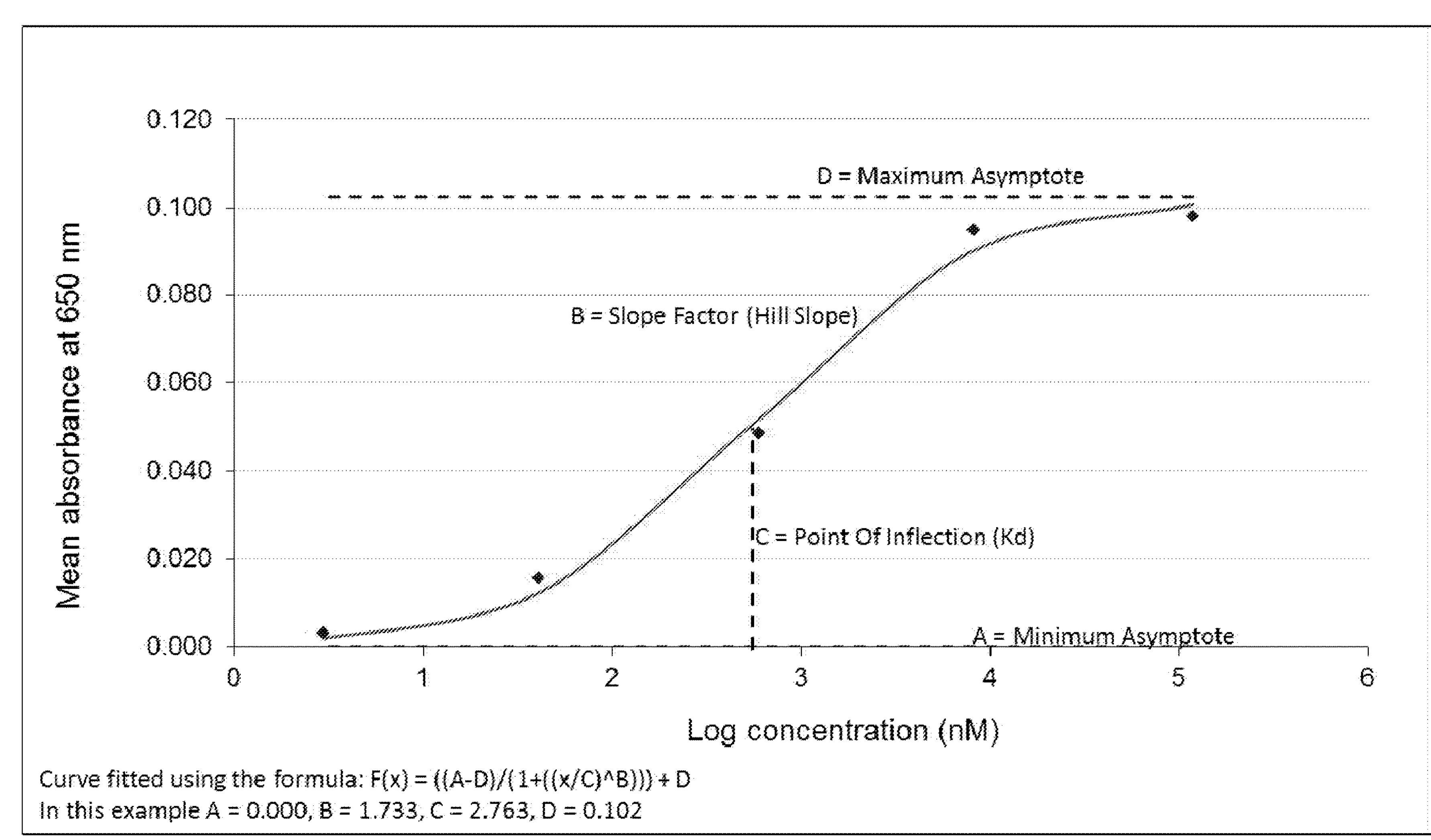
FIG. 1B=dissociation constant (Kd).

The double cut-off method utilises the antigen titration methodology described above. Following detection of the amount of antigen/autoantibody binding at each amount of antigen used in the titration series, and the plotting of a curve of the amount of specific binding versus the amount of antigen for each amount of antigen used in the titration series, a secondary curve parameter is calculated. The secondary curve parameter may be calculated from either a linear or logarithmic regression curve. Herein a secondary curve parameter is any calculated value which provides an indication of the nature of the curve. For example, the secondary curve parameter may be Slope, Intercept, AUC, SlopeMax or dissociation constant (Kd). These secondary curve parameters are illustrated in FIG. 1.

Slope is Calculated Using the Equation:

$$b = \frac{\sum (x-\bar{x})(y-\bar{y})}{\sum (x-\bar{x})^2}$$

where b is the Slope, x refers to the antigen concentration (nM), and y refers to the OD value in absorbance units (AU).

Slope may be calculated from either the linear or logarithmic regression curves, or from both the linear and logarithmic regression curves, for each sample.

Intercept of the regression line is the value of the line at the y-axis when x=0.

Intercept may be calculated from either the linear or logarithmic regression curves, or from both the linear and logarithmic regression curves, for each sample.

AUC may be calculated using the summed trapezoid rule, which may be accomplished by estimating the definite integral between each set of antigen concentrations following the formula:

$$\int_a^b f(x)\,dx \approx (b-a)\left[\frac{f(a)+f(b)}{2}\right].$$

This calculation is repeated for each pair of consecutive antigen concentrations and the resulting values summed to give a total value for AUC.

AUC may be calculated from either the linear or logarithmic regression curves, or from both the linear and logarithmic regression curves, for each sample.

SlopeMax may be calculated using the same formula as the Slope, discussed above. However to determine the greatest possible value for the Slope for each sample, a Slope value is obtained for each pair of consecutive antigen concentrations, with the Slope value of the greatest magnitude representing the SlopeMax.

SlopeMax may be calculated from either the linear or logarithmic regression curves, or from both the linear and logarithmic regression curves, for each sample.

Dissociation constant (Kd) may be calculated by fitting a four parameter logistic curve to each set of titration points and an iterative solve method is used to give values for the minimum asymptote (A), slope factor (B), inflection point (C) and maximum asymptote (D) parameters using the formula $F(x)=((A-D)/(1+((x/C)^B)))+D$, whereby the sum of the squared residuals is minimised. The inflection point for this solved data corresponds to the Kd of the antigen/autoantibody binding.

In certain embodiments the secondary curve parameter may be determined by fitting a logistic curve, such as a 4 parameter logistic curve, to the curve of the amount of specific binding versus the amount of antigen for each amount of antigen used in the titration series. In this embodiment the secondary curve parameter may be Maximum Asymptote, Minimum Asymptote, Hill Slope (or Slope Factor) or Inflection Point.

a 4-Parameter Logistic (4PL) Curve is a Curve Defined by the Formula:

$$F(x)=((A-D)/(1+((x/C)^B)))+D,$$

where A=Minimum Asymptote, B=Hill Slope (or Slope Factor), C=Inflection Point and D=Maximum Asymptote.

To determine secondary curve parameters in this embodiment a 4PL curve is calculated for each sample and antigen using an iterative solve function. Here the 4 parameters are set at values near to the expected value for each, with the following constraints: the value of the Minimum Asymptote is fixed at 0, the value of the Hill Slope is limited to positive values, and the Inflection Point is limited to a maximum value of 1000.

The difference between each point of the titration curve, and the corresponding point on the 4PL curve (returned by the formula $F(x)=((A-D)/(1+((x/C)^B)))+D$) can then be calculated, the differences squared, and the values of all the squared differences summed.

The values used for the 4 secondary curve parameters are then adjusted and the sum of the squared means calculated repeatedly in an iterative manner until the sum of the squared means is as close to zero as possible. The iterative solve may be performed using Microsoft Excel's SOLVER function.

Once a secondary curve parameter has been obtained it will be combined with the antigen/autoantibody binding data in order to determine the presence or absence of the autoantibody. Here, the amount of specific binding between the autoantibody and the antigen will be compared with a predetermined cut-off value as described above.

The cut-off for the secondary curve parameter is determined using known positive samples (e.g. a set of case-control sample sets consisting of a cohort of patients with disease) and known negative samples (e.g. a cohort of normal individuals in case-controlled studies). For each sample a curve of the amount of specific binding versus the amount of antigen for each amount of antigen used in the titration series is plotted, and the secondary curve parameter observed in the known positive sample (e.g. patients with disease) is compared with the secondary curve parameter observed in the known negative sample (e.g. normal individuals). Cut-off values for the secondary curve parameters are chosen that maximise specificity (few false positives) when used in combination with the cut-off for antigen/autoantibody binding discussed above.

Upon calculating the cut-off value for the secondary curve parameter, the directionality required for a positive reading, i.e. whether a value above or below the cut-off is considered positive, is also determined. The directionality required for a positive reading will depend upon the antigen and the secondary curve parameter.

A measurement is considered to be ultimately positive, i.e. indicative of the presence of autoantibody in the test sample, if it is both above the cut-off for antigen/autoantibody binding and demonstrates the directionality required for a positive reading compared to the cut-off for the secondary curve parameter.

As described further in WO2015/193678 (the contents of which are incorporated herein by reference), including a secondary curve parameter in the assay methodology increases specificity of the immunoassay, increasing the Positive Predictive Value (PPV), compared with alternative methods based upon only the amount of specific binding between an autoantibody in the test sample.

It should be understood that although the description of the double cut-off method included herein is focused upon the use of a single secondary curve parameter in combination with measurement of the amount of antigen/autoantibody binding, the use of multiple secondary curve parameters is contemplated. Therefore, in certain embodiments the methods of the invention utilise two, three, four, five, six, seven, eight or more secondary curve parameters.

The double cut-off method is advantageous for use in clinical diagnostic, prognostic, predictive and/or monitoring assays where the absolute amounts of target autoantibody present and the level of binding observed in the absence of the target autoantibody can vary enormously from patient-to-patient. If such assays are based on detection of autoantibody binding using a single amount/concentration of test antigen, patient samples containing an amount of autoantibody which is at the very low or the very high end of the normal physiological range of amount of autoantibody across the population can be missed due to limitations of the assay methodology; samples with a low amount of autoantibody may be scored as false negative results, whereas those with very high levels of autoantibody may be off the scale for accurate detection within the chosen assay methodology. Use of the titration method in combination with the calculation of a secondary curve parameter can account for these differences in autoantibody levels and differences in the level of binding observed.

It should be noted that the double cut-off embodiment may be used with all methods of the invention, including methods of detecting an autoantibody, methods of detecting liver cancer, methods of diagnosing and treating liver cancer, methods of predicting response to an anti-liver cancer treatment and methods of determining an antibody profile. In addition, the double cut off method may be used in embodiments wherein only a single autoantibody is detected as well as in embodiments where a panel of antigens is used to detect multiple autoantibodies. In the panel embodiment it should be noted that the secondary curve parameter calculated for each antigen within the panel need not necessarily be the same. However, in some embodiments the secondary curve parameter calculated for each antigen within the panel may be the same.

Assay Formats

The general features of immunoassays, for example ELISA, radioimmunoassays and the like, are well known to those skilled in the art (see Immunoassay, E. Diamandis and T. Christopoulus, Academic Press, Inc., San Diego, CA, 1996, the contents of which are incorporated herein by reference).

Immunoassays for the detection of autoantibodies having a particular immunological specificity generally require the use of a reagent (antigen) that exhibits specific immunological reactivity with a relevant autoantibody. Depending on the format of the assay this antigen may be immobilised on a solid support. A test sample is brought into contact with the antigen and if autoantibodies of the required immunological specificity are present in the sample they will immunologically react with the antigen to form antigen/autoantibody complexes which may then be detected or quantitatively measured.

The methods of the invention may be carried out in any suitable format which enables contact between a test sample suspected of containing the autoantibody and the antigen. Conveniently, contact between the test sample and the antigen may take place in separate reaction chambers such as the wells of a microtitre plate, allowing different antigens or different amounts of antigen to be assayed in parallel, if required. In embodiments in which varying amounts of the antigen are required, these can be coated onto the wells of the microtitre plate by preparing serial dilutions from a stock of antigen across the wells of the microtitre plate. The stock of antigen may be of known or unknown concentration. Aliquots of the test sample may then be added to the wells of the plate, with the volume and dilution of the test sample kept constant in each well. The absolute amounts of antigen added to the wells of the microtitre plate may vary depending on such factors as the nature of the target autoantibody, the nature of the test sample, dilution of the test sample etc. as will be appreciated by those skilled in the art. Generally, the amounts of antigen and the dilution of the test sample will be selected so as to produce a range of signal strengths which fall within the acceptable detection range of the read-out chosen for detection of antigen/autoantibody binding in the method. Conveniently the tested amounts of antigen may vary in the range of from 1.6 nM to 160 mM.

In a further embodiment of the invention the antigen may be immobilised at a discrete location or reaction site on a solid support. In embodiments where different amounts of the antigen are required, these may each be immobilised at discrete locations or reaction sites on a solid support. The entire support may then be brought into contact with the test sample and binding of autoantibody to antigen detected or measured separately at each of the discrete locations or reaction sites. Suitable solid supports include microarrays. Where different amounts of antigen are required, microarrays can be prepared by immobilising different amounts of a particular antigen at discrete, resolvable reaction sites on the array. In other embodiments the actual amount of immobilised antigen molecules may be kept substantially constant but the size of the sites or spots on the array varied in order to alter the amount of binding epitope available, providing a titration series of sites or spots with different amounts of available binding epitope. In such embodiments the two-dimensional surface concentration of the binding epitope(s) on the antigen is important in preparing the titration series, rather than the absolute amount of antigen. Techniques for the preparation and interrogation of protein/peptide microarrays are generally known in the art.

Microarrays may be used to perform multiple assays for autoantibodies of different specificity on a single sample in parallel. This can be done using arrays comprising multiple antigens or sets of antigens.

Certain antigens may comprise or be derived from proteins or polypeptides isolated from natural sources, including but not limited to proteins or polypeptides isolated from patient tissues or bodily fluids (e.g. plasma, serum, whole blood, urine, sweat, lymph, faeces, cerebrospinal fluid, ascites fluid, pleural effusion, seminal fluid, sputum, nipple aspirate, post-operative seroma and wound drainage fluid). In such embodiments the antigen may comprise substantially all of the naturally occurring protein, i.e. protein substantially in the form in which it is isolated from the natural source, or it may comprise a fragment of the naturally occurring protein. To be effective as an antigen in the method of the invention any such fragment must retain immunological reactivity with the autoantibodies for which it will be used to test. Suitable fragments might, for example, be prepared by chemical or enzymatic cleavage of the isolated protein.

In certain embodiments, and depending on the precise nature of the assay in which it will be used, the antigen may comprise a naturally occurring protein, or fragment thereof, linked to one or more further molecules which impart some desirable characteristic not naturally present in the protein. For example, the protein or fragment may be conjugated to a revealing label, such as for example a fluorescent label, coloured label, luminescent label, radiolabel or heavy metal such as colloidal gold. In other embodiments the protein or fragment may be expressed as a recombinantly produced fusion protein. By way of example, fusion proteins may include a tag peptide at the N- or C-terminus to assist in purification of the recombinantly expressed antigen.

Depending on the format of the assay in which it is to be used the antigen may be immobilised on a solid support such as, for example, a chip, slide, wells of a microtitre plate, bead, membrane or nanoparticle. Immobilisation may be effected via non-covalent adsorption, covalent attachment or via tags.

Any suitable attachment means may be used provided this does not adversely affect the ability of the antigen to immunologically react with the target autoantibody to a significant extent.

The invention is not limited to solid phase assays, but also encompasses assays which, in whole or in part, are carried out in liquid phase, for example solution phase bead assays or competition assays.

In one embodiment, antigens may be labelled with a ligand that would facilitate immobilisation, such as biotin. The antigen can then be diluted to a suitable titration range and allowed to react with autoantibodies in patient samples in solution. The resulting immune complexes can then be immobilised on to a solid support via a ligand-receptor interaction (e.g. biotin-streptavidin) and the remainder of the assay performed as described below.

To facilitate the production of biotinylated antigens for use in the assay methods of the invention, cDNAs encoding a full length antigen, a truncated version thereof or an antigenic fragment thereof may be expressed as a fusion protein labelled with a protein or polypeptide tag to which the biotin co-factor may be attached, for example via an enzymatic reaction.

Vectors for the production of recombinant biotinylated antigens are commercially available from a number of sources. Alternatively, biotinylated antigens may be produced by covalent linkage of biotin to the antigen molecule following expression and purification.

As aforesaid, the immunoassay used to detect autoantibodies according to the invention may be based on standard techniques known in the art. In a most preferred embodiment the immunoassay may be an ELISA. ELISAs are generally well known in the art. In a typical indirect ELISA an antigen having specificity for the autoantibodies under test is immobilised on a solid surface (e.g. the wells of a standard microtiter assay plate, or the surface of a microbead or a microarray) and a sample comprising bodily fluid to be tested for the presence of autoantibodies is brought into contact with the immobilised antigen. Any autoantibodies of the desired specificity present in the sample will bind to the immobilised antigen. The bound antigen/autoantibody complexes may then be detected using any suitable method. In one preferred embodiment a labelled secondary anti-human immunoglobulin antibody, which specifically recognises an epitope common to one or more classes of human immunoglobulins, is used to detect the antigen/autoantibody complexes. Typically the secondary antibody will be anti-IgG or anti-IgM. The secondary antibody is usually labelled with a detectable marker, typically an enzyme marker such as, for example, peroxidase or alkaline phosphatase, allowing quantitative detection by the addition of a substrate for the enzyme which generates a detectable product, for example a coloured, chemiluminescent or fluorescent product. Other types of detectable labels known in the art may be used with equivalent effect.

Applications of the Method of the Invention

The present invention provides use of a tumour marker antigen selected from the group consisting of MMP9, AIF1, EpCAM and CDKN1B in a method of detecting liver cancer in a mammalian subject by detecting an autoantibody immunologically specific for MMP9, AIF1, EpCAM or CDKN1B in a test sample comprising a bodily fluid from the mammalian subject, which method comprises the steps of:

(a) contacting the test sample with a tumour marker antigen selected from the group consisting of MMP9, AIF1, EpCAM and CDKN1B; and
(b) determining the presence or absence of complexes of the tumour marker antigen bound to autoantibodies present in the test sample;

whereby the presence of said complexes is indicative of the presence of liver cancer.

Within this embodiment of the invention all limitations discussed above in relation to the various methods of the invention are contemplated in relation to this use.

Assay methods according to the invention may be employed in a variety of different clinical situations. In particular, the method may be used in the detection or diagnosis of liver cancer, in assessing the prognosis of a patient diagnosed with liver cancer, in predicting response to therapy, in monitoring the progress of liver cancer in a patient, in screening a population of asymptomatic human subjects in order to diagnose the presence of liver cancer, in predicting the response of a liver cancer patient to anti-liver cancer treatment (e.g. chemotherapy, radiofrequency ablation, liver resection, liver transplant, vaccination, anti-growth factor or signal transduction therapies, endocrine therapy, human antibody therapy, transcatheter arterial chemoembolization, percutaneous ethanol injection, microwave ablation, sorafenib administration and radioembolisation), in monitoring the response of a liver cancer patient to anti-liver cancer treatment (e.g. chemotherapy, radiofrequency ablation, liver resection, liver transplant, vaccination, anti-growth factor or signal transduction therapies, endocrine therapy, human antibody therapy, transcatheter arterial chemoembolization, percutaneous ethanol injection, microwave ablation, sorafenib administration and radioembolisation), in the detection of recurrent disease in a patient previously diagnosed as having liver cancer who has undergone anti-liver cancer treatment to reduce the amount of liver cancer present, in the selection of an anti-liver cancer therapy (e.g. chemotherapy, radiofrequency ablation, liver resection, liver transplant, vaccination, anti-growth factor or signal transduction therapies, endocrine therapy, human antibody therapy, transcatheter arterial chemoembolization, percutaneous ethanol injection, microwave ablation, sorafenib administration and radioembolisation) for use in a particular patient or in determining an antibody profile in a patient having or suspected of having liver cancer.

Kits

The present invention encompasses a kit suitable for performing any one of the methods of the invention, wherein the kit comprises:

(a) one or more tumour marker antigens; and
(b) a reagent capable of detecting complexes of the tumour marker antigen bound to autoantibodies present in the test sample.

The invention also encompasses a kit for the detection of autoantibodies in a test sample comprising a bodily fluid from a mammalian subject comprising:

(a) a tumour marker antigen selected from the group consisting of MMP9, AIF1 EpCAM and CDKN1B; and
(b) a reagent capable of detecting complexes of the tumour marker antigen bound to autoantibodies present in the test sample.

In Certain Embodiments the Kit May Further Comprise:

(c) means for contacting the tumour marker antigen with a test sample comprising a bodily fluid from a mammalian subject.

Examples of means for contacting the tumour marker antigen with a test sample comprising a bodily fluid from a mammalian subject include the immobilisation of the tumour marker antigen on a chip, slide, wells of a microtitre plate, bead, membrane or nanoparticle.

In some embodiments the tumour marker antigen within the kit may be present within a panel of two or more tumour marker antigens. Within this embodiment the kit may comprise two, three, four, five, six, seven, eight, nine, ten, eleven, twelve, thirteen, fourteen, fifteen, sixteen, seventeen, eighteen, nineteen, twenty, twenty one, twenty two, twenty three, twenty four, twenty five, twenty six, twenty seven, twenty eight, twenty nine, thirty, thirty one, thirty two, thirty three, thirty four, thirty five, thirty six, thirty seven, thirty eight or more antigens. These antigens may be distinct antigens, wherein distinct antigens are antigens derived from different proteins or polypeptides (such as antigens derived from unrelated proteins encoded by different genes) or antigens which are derived from different peptide epitopes of a single protein or polypeptide, as defined above.

In one embodiment the panel of two or more tumour marker antigens may comprise MMP9, AIF1, EpCAM and CDKN1B. In a certain specific embodiment, the panel may consist of MMP9, AIF1, EpCAM and CDKN1B.

In one embodiment, the panel of two or more tumour marker antigens may comprise one or more tumour marker antigens selected from the group consisting of NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1. Within this embodiment the panel may comprise one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four, twenty five, twenty six, twenty seven, twenty eight, twenty nine, thirty, thirty one, thirty two, thirty three or thirty four of the recited tumour marker antigens. In accordance with the invention, the panel will also comprise MMP9, AIF1, EpCAM or CDKN1B and may comprise one, two, three or four of these tumour marker antigens. In embodiments where two or three of these tumour marker antigens are included in the panel, all combinations of two or three of these antigens are contemplated. In specific embodiments the panel may comprise MMP9, AIF1, EpCAM and CDKN1B.

In one embodiment, the panel of two or more tumour marker antigens may comprise MMP9, AIF1, EpCAM, NY-ESO-1, HSPA4, vimentin, HNRNP-L and transferrin. In another embodiment the panel of two or more tumour marker antigens may consist of MMP9, AIF1, EpCAM, NY-ESO-1, HSPA4, vimentin, HNRNP-L and transferrin.

In another embodiment, the panel of two or more tumour marker antigens may comprise AIF1, EpCAM, HSPA4 and CPS1. In another embodiment the panel of two or more tumour marker antigens may consist of AIF1, EpCAM, HSPA4 and CPS1.

In a further embodiment, the panel of two or more tumour marker antigens may comprise EpCAM, NY-ESO-1, vimentin, HSPA2, HSPA4 and HNRNP-L. In another embodiment the panel of two or more tumour marker antigens may consist of EpCAM, NY-ESO-1, vimentin, HSPA2, HSPA4 and HNRNP-L.

In a still further embodiment, the panel of two or more tumour marker antigens may comprise MMP9, AIF1, EpCAM, DDX3X, SALL4, MAGE A4, NY-ESO-1, CAGE, RalA and SOX2. In another embodiment the panel of two or more tumour marker antigens may consist of MMP9, AIF1, EpCAM, DDX3X, SALL4, MAGE A4, NY-ESO-1, CAGE, RalA and SOX2.

In a still further embodiment, the panel of two or more tumour marker antigens may comprise EpCAM, CAGE, SOX2, RalA, MAGE A4, DDX3X and NY-ESO-1. In another embodiment the panel of two or more tumour marker antigens may consist of EpCAM, CAGE, SOX2, RalA, MAGE A4, DDX3X and NY-ESO-1.

In a still further embodiment, the panel of two or more tumour marker antigens may comprise AIF1, CAGE, HSPD1, SOX2, SALL4, HSPA4 and transferrin. In another embodiment the panel of two or more tumour marker antigens may consist of AIF1, CAGE, HSPD1, SOX2, SALL4, HSPA4 and transferrin.

In a specific embodiment, the panel of two or more tumour marker antigens may comprise NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1. In accordance with the invention, the panel will also comprise MMP9, AIF1, EpCAM or CDKN1B and may comprise one, two, three or four of these tumour marker antigens. In embodiments where two or three of these tumour marker antigens are included in the panel, all combinations of two or three of these antigens are contemplated. In specific embodiments the panel may comprise MMP9, AIF1, EpCAM and CDKN1B. For example, the panel of two or more tumour marker antigens may comprise MMP9, AIF1, EpCAM, CDKN1B, NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1. Alternatively, the panel of two or more tumour marker antigens may consist of MMP9, AIF1, EpCAM, CDKN1B, NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1.

In a specific embodiment the panel of two or more tumour marker antigens may comprise CAGE, NY-ESO-1, MMP9, transferrin, MAGE A4, RalA, HSPA4, SALL4, Cyclin B1, EpCAM, DDX3X, and AIF1. In another embodiment the panel of two or more tumour marker antigens may consist of CAGE, NY-ESO-1, MMP9, transferrin, MAGE A4, RalA, HSPA4, SALL4, Cyclin B1, EpCAM, DDX3X, and AIF1.

In a specific embodiment the panel of two or more tumour marker antigens may comprise CAGE, NY-ESO-1, MMP9, transferrin, MAGE A4, RalA, HSPA4, SALL4, Cyclin B1, EpCAM, DDX3X, AIF1, SOX2 and AFP. In another embodiment the panel of two or more tumour marker antigens may consist of CAGE, NY-ESO-1, MMP9, transferrin, MAGE A4, RalA, HSPA4, SALL4, Cyclin B1, EpCAM, DDX3X, AIF1 SOX2 and AFP.

The kit of the invention may be suitable for the detection of liver cancer.

In certain embodiments the kit may be for the detection of liver cancer.

Within the kits of the invention, the bodily fluid may be selected from the group consisting of plasma, serum, whole blood, urine, sweat, lymph, faeces, cerebrospinal fluid, ascites fluid, pleural effusion, seminal fluid, sputum, nipple aspirate, post-operative seroma, saliva, amniotic fluid, tears and wound drainage fluid.

The invention will be further understood with reference to the following non-limiting experimental examples.

EXAMPLES

Example 1

General Protocol for Measuring Autoantibodies to Tumour-Associated Proteins

Samples of tumour marker antigens may be prepared by recombinant expression, following analogous methods to those described in WO 99/58978 (the contents of which are incorporated herein by reference). Briefly, cDNAs encoding the marker antigens of interest were cloned into the pET21 vector (Invitrogen) modified to encode a biotin tag and a 6× histidine tag to aid in purification of the expressed protein. The resulting clones were grown in BL21(DE3) *E coli*, with the bacteria subsequently lysed. The expressed antigens were recovered via nickel chelate affinity columns (HiTrap, commercially available from GE Healthcare), following manufacturer's protocol. The purity, specificity and yield of expressed protein assessed by SDS-PAGE, Western blot and protein assay prior to storage.

A negative control protein, VOL, was produced by transforming BL21(DE3) *E coli* with empty pET21 vector (i.e. no cDNA encoding tumour associated antigen). The expressed and purified protein includes the same His and biotin tag sequences found on the recombinant tumour associated antigens and allows correction for non-specific autoantibody binding to residual bacterial contaminants.

GenBank Accession Numbers for a Number of Marker cDNAs are as Follows:

AFP: NM_001134.1
AIF1: NM_001623.3
AKR1B10: NM_020299.4.
APOA1: NM_000039.1.
BCL2: NM_000633.2
CAGE: NM_182699
CALR: NM_004343.3
CD44: NM_001001389
CDKN1B: NM_004064.4
CK18: NM_000224
CPS1: NM_001875.4
CCNB1: NM_031966.2
CYCLIN B1: NM_031966.2
DDX3X: NM_001356.3
ECAM: NM_002354
FUCA1: NM_000147.4
GLUL: NM_001033044.2
HNRNP-A2: NM_002137.3
HNRNP-L: NM_001533.2
HSPA2: NM_021979.3.
HSPA4: NM_002154.3
HSPD1: NM_002156.4
IL8: NM_000584.3
MAGE A4: NM_001011548.1
MDM2: NM_002392.5
MMP9: NM_004994.2.
NPM1: NM_002520.6
NY-ESO-1: NM_001327
PEBP1: NM_002567.2
P62: NM_001007225.1
Prolactin: NM_000948.5
RalA: NM_005402.2
RGN: NM_004683.5
SALL4: NM_020436.3.
SOX2: NM_003106
SPP1: NM_001040058.1
SSX2: NM_175698.1
TGFB1: NM_000660.5
Transferrin: NM_001063.3
Vimentin: NM_003380.3
YWHAZ: NM_001135699.1

Figure 2B:
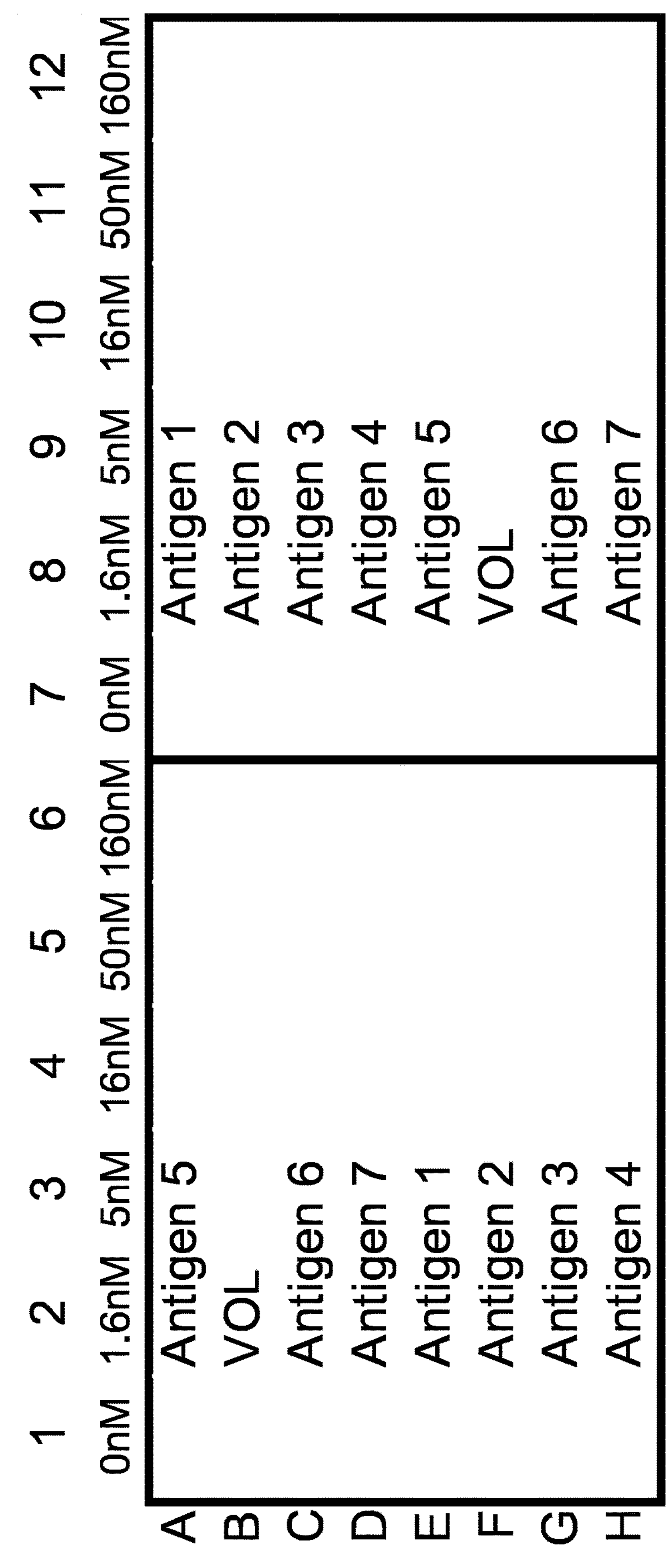
FIG. 2B=titration layout.

Antigens and VOL (negative control) were diluted to appropriate concentrations in high phosphate binding buffer then diluted to provide either two separate protein concentrations, as in the high throughput assay (HTPA) format (FIG. 2A), or a semi-log titration range, as in the titration assay format (FIG. 2B). Antigen dilutions were dispensed at 50 μl/well into the rows of a Falcon microtitre plate according to the plate layout (FIGS. 2A and 2B) using an automated liquid handling system. Plates were covered and stored at 18-22° C. for 18-24 h.

Plates were blocked with pig skin gelatin binding buffer (PSGBB, PBS+0.1% pig skin gelatine+0.05% sodium azide) at 200 μl/well for one hour. Serum samples were defrosted, vortexed and diluted 1/110 in PSGBB at 18-22° C. Plates were aspirated and tapped dry on tissue paper. Each diluted serum sample was dispensed at 50 μl/well into all wells of the microtitre plate using an automated liquid handling instrument. Plates were covered and incubated for 1.5 hours at room temperature with shaking.

Wash step: Plates were washed three times in PBS+0.1% tween 20 using an automated plate washer then tapped dry on tissue paper.

Horseradish peroxidase conjugated rabbit anti-human immunoglobulin (Dako, 1/5,000 in PSGBB) was dispensed at 50 μl/well into all wells of the microtitre plates. Plates were then incubated at room temperature for 1 hour with shaking. Plates were washed as described above.

Pre-prepared TMB substrate was added to each plate at 50 μl/well and incubated on the bench for 15 minutes. Plates were gently tapped to mix. The optical density of each well was determined at 650 nm using a standard spectrophotometric plate reader.

Example 2

Detection of Autoantibodies in Hepatocellular Carcinoma (HCC) by HTPA

The following data were obtained from a pilot study to assess the sensitivity and specificity of a panel of autoantibody assays in the detection of HCC using the HTPA format. The clinical and demographic status of subjects included in the study is given in Tables 1-4.

TABLE 1

Demographic status of patients included in the study described in Example 2

| Demographic factor | HCC patients | Benign liver disease patients | Individuals with no evidence of malignancy |
|---|---|---|---|
| Number | 99 | 99 | 99 |
| Mean age | 62.3 | 58.1 | 62.2 |
| Age range | 30-91 | 30-89 | 30-87 |
| % Male | 69 | 69 | 69 |

TABLE 2

Size of the primary tumour present in the HCC patients

| | Number of patients available | Mean | Min-Max |
|---|---|---|---|
| Primary tumour size (cm) | 88 | 5.9 | 0.4-19 |

TABLE 3

Tumour stage of the HCC patients using TNM staging

| TNM stage | Number |
|---|---|
| 1 | 35 |
| 2 | 21 |
| 3 | 21 |
| 4 | 2 |
| N/A | 20 |

TNM = TNM Classification of Malignant Tumours staging system;
N/A = not available

TABLE 4

Liver disease present in the benign liver disease patients

| Benign background | Number |
|---|---|
| Hepatitis C viral infection | 67 |
| Hepatitis B viral infection | 22 |
| Alcoholic Liver Disease | 6 |

TABLE 4-continued

| Liver disease present in the benign liver disease patients | |
|---|---|
| Benign background | Number |
| Autoimmune Hepatitis | 2 |
| Haemochromatosis | 1 |
| Primary Biliary Cirrhosis | 1 |
| Total | 99 |

The assay was carried out according to the protocol given in Example 1 using the antigens listed in Table 5. The assay cut-off was determined by selecting the cut-off value giving the largest Youden's value whilst keeping individual marker specificity greater than 90%. The results are shown in Table 5 and it is apparent that a number of these autoantibody markers demonstrate higher levels of positivity in patients with HCC than those with benign liver disease or healthy controls, thus they may have the ability to distinguish HCC patients from patients with no evidence of malignancy.

Furthermore, it is apparent that measurement of a panel of AAbs increases the ability to distinguish HCC patients from those with non-cancerous liver disease compared to any single AAb alone. Panels 1 and 2 (Tables 6 and 10) show how it is possible to combine different sets of AAbs to achieve similar performances whilst optimising certain characteristics to suit varying clinical needs. Panel 1 (Table 6) contains markers useful for all patients. Optimising the markers included in panels by gender, as in Panel 2 (Table 10), increases specificity compared to Panel 1 with a slight reduction in sensitivity. This demonstrates the ability to build different panels to suit varying clinical needs. Tables 7 and 11 show that each of the panels can detect patients with stage 1 and 2 cancers, which is crucial early diagnosis leading to effective treatment of HCC.

TABLE 5

| Positivity of individual AAb markers in each group | | | | | | |
|---|---|---|---|---|---|---|
| | HCC | | Benign | | Normal | |
| | Positives | % | Positives | % | Positives | % |
| AIF1 | 2 | 2.0 | 0 | 0 | 0 | 0 |
| AKR1B10 | 1 | 1.0 | 0 | 0 | 0 | 0 |
| ApoA1 | 1 | 1.0 | 0 | 0 | 0 | 0 |
| BCL2 | 3 | 3.0 | 1 | 1.0 | 1 | 1.0 |
| CD44 | 1 | 1.0 | 0 | 0 | 0 | 0 |
| CDKN1B | 2 | 2.0 | 0 | 0 | 1 | 1.0 |
| CK18 | 1 | 1.0 | 0 | 0 | 0 | 0 |
| CPS1 | 2 | 2.0 | 1 | 1.0 | 0 | 0 |
| DDX3X | 3 | 3.0 | 1 | 1.0 | 2 | 2.0 |
| EpCAM | 5 | 5.1 | 1 | 1.0 | 6 | 6.1 |
| FUCA1 | 1 | 1.0 | 0 | 0 | 0 | 0 |
| GLUL | 1 | 1.0 | 0 | 0 | 0 | 0 |
| HNRNP-A2 | 1 | 1.0 | 0 | 0 | 0 | 0 |
| HNRNP-L | 3 | 3.0 | 2 | 2.0 | 0 | 0 |
| HSPA2 | 1 | 1.0 | 0 | 0 | 0 | 0 |
| HSPA4 | 5 | 5.1 | 1 | 1.0 | 0 | 0 |
| HSPD1 | 2 | 2.0 | 2 | 2.0 | 0 | 0 |
| IL-8 | 5 | 5.1 | 4 | 4.0 | 4 | 4.0 |
| MDM2 | 2 | 2.0 | 1 | 1.0 | 0 | 0 |
| MMP9 | 3 | 3.0 | 1 | 1.0 | 1 | 1.0 |
| NPM1 | 2 | 2.0 | 1 | 1.0 | 0 | 0 |
| NY-ESO-1 | 7 | 7.1 | 0 | 0 | 1 | 1.0 |
| PEBP1 | 1 | 1.0 | 0 | 0 | 0 | 0 |
| Prolactin | 2 | 2.0 | 1 | 1.0 | 1 | 1.0 |

TABLE 5-continued

| Positivity of individual AAb markers in each group | | | | | | |
|---|---|---|---|---|---|---|
| | HCC | | Benign | | Normal | |
| | Positives | % | Positives | % | Positives | % |
| RGN | 1 | 1.0 | 0 | 0 | 0 | 0 |
| SALL4 | 1 | 1.0 | 0 | 0 | 0 | 0 |
| SPP1 | 1 | 1.0 | 1 | 1.0 | 0 | 0 |
| SSX2 | 3 | 3.0 | 1 | 1.0 | 1 | 1.0 |
| TF | 2 | 2.0 | 0 | 0 | 0 | 0 |
| TGFB1 | 1 | 1.0 | 0 | 0 | 0 | 0 |
| Vimentin | 7 | 7.1 | 3 | 3.0 | 6 | 6.1 |
| YWHAZ | 2 | 2.0 | 1 | 1.0 | 2 | 2.0 |

Panel 1—General Panel

Panel 1 was formed using NRI (Net Reclassification Improvement) and contains the tumour marker antigens EpCAM, AIF1 and MMP9 along with NY-ESO-1, HSPA4, vimentin, HNRNP-L and transferrin wherein the result is positive if any of the given AAb levels is above its cut-off generated as described in Example 2. Tables 6 and 7 show the performance of the panel in the sample set described in Example 2.

TABLE 6

| Performance and make-up of Panel 1 | | | |
|---|---|---|---|
| Panel 1 | Sensitivity (%) | Specificity benign (%) | Specificity normal (%) |
| NY-ESO-1, EpCAM, HSPA4, vimentin, HNRNP-L, transferrin, AIF1, MMP9 | 28.3 | 94 | 87.9 |

TABLE 7

| Performance of Panel 1 by TNM stage | | | |
|---|---|---|---|
| Stage | Positive | Negative | Sensitivity |
| 1 | 8 | 27 | 23 |
| 2 | 4 | 17 | 19 |
| 3 | 8 | 13 | 38 |
| 4 | 0 | 2 | 0 |

Panel 2—Individual Panels for Men and Women

Panel 2 was formed by splitting the sample set described in Example 2 into separate gender groups and performing a separate NRI for each group. Panel 2 contains the tumour marker antigens EpCAM, AIF1 and MMP9 along with HSPA4, CPS1, NY-ESO-1, vimentin, HSPA2 and HNRNP-L. The result is positive if the patient is female and any of HSPA4, AIF1, EpCAM or CPS1 are above the cut-off generated as described in Example 2, or if the patient is male and any of NY-ESO-1, vimentin, EpCAM, HSPA2, HSPA4 or HNRNP-L are above the cut-off generated as described in Example 2. Tables 10 and 11 show the performance of Panel 2 in the sample set described in Example 2.

TABLE 8

| Performance and make-up of Panel 2a-Women | | | |
|---|---|---|---|
| Panel 2a | Sensitivity (%) | Specificity benign (%) | Specificity normal (%) |
| HSPA4, AIF1 EpCAM, CPS1 | 22.6 | 100 | 100 |

TABLE 9

| Performance and make-up of Panel 2b-Men | | | |
|---|---|---|---|
| Panel 2b | Sensitivity (%) | Specificity benign (%) | Specificity normal (%) |
| NY-ESO-1, vimentin, EpCAM, HSPA2, HSPA4, HNRNP-L | 25 | 97.1 | 92.6 |

TABLE 10

| Performance and make-up of Panel 2-Combined | | | |
|---|---|---|---|
| Panel 2 | Sensitivity (%) | Specificity benign (%) | Specificity normal (%) |
| 2a + 2b | 24.2 | 98 | 94.9 |

TABLE 11

| Performance of Panel 2 by TNM stage | | | |
|---|---|---|---|
| Stage | Positive | Negative | Sensitivity (%) |
| 1 | 6 | 29 | 17.1 |
| 2 | 4 | 17 | 19 |
| 3 | 6 | 15 | 28.6 |
| 4 | 0 | 2 | 0 |

Example 3

Additional Measurement of AFP in Combination with Autoantibodies Measured by HTPA Circulating alpha-fetoprotein (AFP) was measured in the serum samples for the sample set described in Example 2 using a commercially available ELISA (Aviva Systems Biology). A commonly-used cut-off of 200 ng/ml was applied to assess positivity. Table 12 shows the results of adding AFP to Panels 1 and 2 shown in Example 2. It is clear from these results that the performance of AFP in combination with the AAb panels is greater than the performance of either AFP or the AAb panels alone.

TABLE 12

| Performance of AFP alone and when added to the panels described in Example 2 | | | |
|---|---|---|---|
| Marker combination | Sensitivity | Specificity benign | Specificity normal |
| AFP | 35.4 | 100 | 100 |
| Panel 1 + AFP | 52.5 | 93.9 | 87.9 |
| Panel 2 (combined) + AFP | 49.5 | 97.9 | 94.9 |

Example 4

Detection of Autoantibodies in Hepatocellular Carcinoma (HCC) by Titration Assay The following data was obtained from a study to assess the sensitivity and specificity of a panel of autoantibody assays in detection of HCC using the titration plate format (FIG. 2B). The clinical and demographic status of subjects included in the study is given in Tables 13-16.

TABLE 13

| Demographic status of patients included in the study described in Example 4 | | | |
|---|---|---|---|
| Demographic factor | HCC patients | Benign liver disease patients | Individuals with no evidence of malignancy |
| Number | 98 | 99 | 95 |
| Mean age | 62.6 | 50.7 | 62.7 |
| Age range | 30-91 | 30-82 | 30-84 |
| % Male | 69 | 69 | 68 |

TABLE 14

| Size of the primary tumour present in the HCC patients | | | |
|---|---|---|---|
| | Number of patients available | Mean | Min-Max |
| Primary tumour size (cm) | 86 | 6.02 | 0.4-19 |

TABLE 15

| Tumour stage of the HCC patients using TNM staging | |
|---|---|
| TNM stage | Number |
| 1 | 35 |
| 2 | 20 |
| 3 | 21 |
| 4 | 2 |
| N/A | 20 |

N/A = not applicable

TABLE 16

| Liver disease present in the benign liver disease patients | |
|---|---|
| Benign background | Number |
| Hepatitis C viral infection | 58 |
| Hepatitis B viral infection | 31 |
| Alcoholic Liver Disease | 6 |
| Autoimmune Hepatitis | 2 |
| Haemochromatosis | 1 |
| Primary Biliary Cirrhosis | 1 |
| Total | 99 |

The assay was carried out according to the protocol given in Example 1 using the antigens listed in Table 17. The assay cut-off was determined by selecting the cut-off value giving the largest Youden's value whilst keeping individual marker specificity greater than 90%. The results are shown in Table 17 and it is apparent that some of these autoantibody markers demonstrate higher levels of positivity in patients with HCC than those with benign liver disease or healthy controls thus they may have the ability to distinguish HCC from patients with no evidence of malignant disease. The AAbs found to demonstrate cancer/normal differentiation in the study shown in Example 2 continue to show an ability to distinguish HCC patients from patients with non-cancerous liver disease (Benign) and healthy controls (Normal). Furthermore, it is apparent that measurement of a panel again increases the ability to distinguish HCC patients compared to any single marker alone.

Panel 3 (Table 18) and Panel 4 (Table 22) show how it is possible to combine different sets of markers to achieve similar performances whilst optimising certain characteristics to suit varying clinical needs. Panel 3 contains markers useable for all patients, whilst Panel 4 specifies different markers by gender which increases specificity whilst maintaining sensitivity (Tables 20 and 21). This demonstrates the ability to build different panels to suit varying clinical needs. Each of the example panels can detect patients with stage 1 and 2 cancers which is crucial for early diagnosis and hence effective treatment of HCC (Tables 19 and 23).

TABLE 17

Positivity of individual AAb markers in each group

| | HCC | | Benign | | Normal | |
|---|---|---|---|---|---|---|
| | Positives | % | Positives | % | Positives | % |
| AIF1 | 1 | 1.0 | 0 | 0 | 0 | 0 |
| CAGE | 12 | 12.2 | 3 | 3.0 | 9 | 9.5 |
| CDKN1B | 14 | 14.3 | 13 | 13.0 | 21 | 22.1 |
| DDX3X | 5 | 5.1 | 2 | 2.0 | 2 | 2.1 |
| EpCAM | 3 | 3.1 | 0 | 0 | 3 | 3.2 |
| HNRNP-A2 | 6 | 6.1 | 4 | 4.0 | 6 | 6.3 |
| HSPA4 | 4 | 4.1 | 1 | 1.0 | 0 | 0 |
| HSPD1 | 7 | 7.1 | 5 | 5.0 | 3 | 3.2 |
| MAGE A4 | 3 | 3.1 | 0 | 0 | 0 | 0 |
| MMP9 | 2 | 2.0 | 1 | 1.0 | 0 | 0 |
| NY-ESO-1 | 8 | 8.2 | 0 | 0 | 4 | 4.2 |
| p62 | 9 | 9.2 | 5 | 5.0 | 2 | 2.1 |
| RalA | 4 | 4.1 | 1 | 1.0 | 4 | 4.2 |
| SALL4 | 6 | 6.1 | 3 | 3.0 | 1 | 1.1 |
| SOX2 | 3 | 3.1 | 0 | 0 | 1 | 1.1 |
| Transferrin | 7 | 7.1 | 5 | 5.0 | 1 | 1.1 |
| YWHAZ | 6 | (6.1) | 4 | (4.0) | 5 | (5.3) |

Panel 3

Panel 3 was formed using NRI and contains the tumour marker antigens EpCAM, AIF1 and MMP9 along with DDX3X, SALL4, MAGE A4, NY-ESO-1, CAGE, RalA and SOX2, wherein the result is positive if any of the given AAb levels is above its cut-off generated as described in Example 4. Tables 18 and 19 show the performance of the panel in the sample set described in Example 4.

TABLE 18

Performance and make-up of Panel 3

| | Sensitivity (%) | Specificity benign (%) | Specificity normals (%) |
|---|---|---|---|
| DDX3X, SALL4, MAGE A4, MMP9, AIF1, NY-ESO-1, CAGE, RalA, EpCAM, SOX2 | 36.7 | 89.9 | 84.2 |

TABLE 19

Performance of Panel 3 by TNM stage

| Stage | Positive | Negative | Sensitivity (%) |
|---|---|---|---|
| 1 | 10 | 25 | 28.6 |
| 2 | 8 | 12 | 40 |
| 3 | 8 | 13 | 38 |
| 4 | 1 | 1 | 100 |

Panel 4—Individual Panel for Men and Women

Panel 4 was formed by splitting the sample set described in Example 2 into separate gender groups and performing a separate NRI for each group. Panel 4 contains the tumour marker antigens EpCAM and AIF1 along with CAGE, SOX2, RalA, MAGE A4, DDX3X, NY-ESO-1, HSPD1, SALL4, HSPA4 and transferrin. The result is positive if the patient is female and any of CAGE, HSPD1, SOX2, SALL4, AIF1, HSPA4 or transferrin are above the cut-off generated as described in Example 4, or if the patient is male and any of CAGE, SOX2, RalA, MAGE A4, DDX3X, NY-ESO-1 or EpCAM are above the cut-off generated as described in Example 4. Tables 10 and 11 show the performance of Panel 4 in the sample set described in Example 4.

TABLE 20

Performance and make-up of Panel 4a—Men

| | Sensitivity (%) | Specificity benign (%) | Specificity normals (%) |
|---|---|---|---|
| CAGE, SOX2, RalA, MAGE A4, DDX3X, NY-ESO-1, EpCAM | 32.4 | 95.6 | 86.2 |

TABLE 21

Performance and make-up of Panel 4b—Women

| | Sensitivity (%) | Specificity benign (%) | Specificity normals (%) |
|---|---|---|---|
| CAGE, HSPD1, SOX2, SALL4, AIF1, HSPA4, transferrin | 50 | 90.3 | 90 |

TABLE 22

Performance and make-up of Panel 4—Combined

| | Sensitivity (%) | Specificity benign (%) | Specificity normals (%) |
|---|---|---|---|
| 4a + 4b | 37 | 93.8 | 87.4 |

TABLE 23

| Performance of Panel 4 by TNM stage | | | |
|---|---|---|---|
| Stage | Positive | Negative | Sensitivity (%) |
| 1 | 12 | 23 | 34.3 |
| 2 | 7 | 13 | 35 |
| 3 | 7 | 14 | 30 |
| 4 | 1 | 1 | 50 |

Example 5

Additional Measurement of AFP in Combination with Autoantibodies Measured by Titration Assay Circulating alpha-fetoprotein (AFP) was measured in the serum samples for the sample set described in Example 4 using a commercially available ELISA (Aviva Systems Biology). A commonly-used cut-off of 200 ng/ml was applied to assess positivity. Table 24 shows the results of adding AFP to Panels 3 and 4 shown in Example 4. It is clear from these results that the performance of AFP in combination with the AAb panels is greater than the performance of either AFP or the AAb panels alone.

TABLE 24

| Performance of AFP alone and when added to the panels described in Example 4 | | | |
|---|---|---|---|
| Marker combination | Sensitivity (%) | Specificity benign (%) | Specificity normal (%) |
| AFP | 31.6 | 100 | 100 |
| Panel 3 + AFP | 55.1 | 89.9 | 84.2 |
| Panel 4 (combined) + AFP | 55.1 | 93.8 | 87.4 |

Example 6

Training Study for Design & Development of EarlyCDT-Liver LDT

The following data was obtained from a study to assess the sensitivity and specificity of a panel of autoantibody assays in detection of HCC using the titration plate format (FIG. 2B). The demographic status of subjects and the cirrhotic status of the benign cohort is given in Tables 25-26, a different cohort than those used in the previous examples.

TABLE 25

| Demographic status of patient cohort used in Example 6 | | | |
|---|---|---|---|
| Demographic factor | HCC patients (HCC) | Benign liver disease patients (Benign) | Individuals with no evidence of malignancy (Normal) |
| Number | 169 | 184 | 191 |
| Mean age (age range) | 59.8(32-81) | 54.7(20-76) | 59.9(31-81) |
| % Male | 85.2 | 70.1 | 84.3 |

TABLE 26

| Cirrhotic status of the benign cohort patients | |
|---|---|
| Cirrhotic Status | Number |
| Cirrhotic | 87 |
| Non-Cirrhotic liver disease | 81 |
| Unknown | 16 |
| Total | 184 |

The assay was carried out according to the protocol given in Example 1 using the antigens listed in Table 27. Cut-offs for each marker were determined by applying a Monte Carlo direct search method constraining specificity to >85%. The results are shown in Table 27 and it is apparent that some of these autoantibody markers demonstrate higher levels of positivity in patients with HCC than those in the benign or normal cohorts, thus they have the ability to distinguish HCC from patients with no evidence of malignant disease. AAbs found to demonstrate cancer/normal differentiation in the study shown in Example 2 continue to show an ability to distinguish HCC patients from patients with non-cancerous liver disease (Benign) and healthy controls (Normal). Furthermore, it is apparent that measurement of a panel again increases the ability to distinguish HCC patients compared to any single marker alone. The panel can detect patients with stage 1 and 2 cancers, with sensitivities of 40-45%, which is crucial for early diagnosis and hence effective treatment of HCC (Table 28).

TABLE 27

| Positivity of individual AAb markers in each group | | | | | | |
|---|---|---|---|---|---|---|
| | HCC | | Benign | | Normal | |
| Autoantibody | Positives | (%) | Positives | (%) | Positives | (%) |
| AIF1 | 2 | 1.2 | 0 | 0.0 | 0 | 0.0 |
| CAGE | 33 | 19.5 | 7 | 3.8 | 5 | 2.6 |
| CYCLIN B1 | 8 | 4.7 | 8 | 4.3 | 2 | 1.0 |
| DDX3X | 3 | 1.8 | 0 | 0.0 | 0 | 0.0 |
| EpCAM | 5 | 3.0 | 2 | 1.1 | 1 | 0.5 |
| HSPA4 | 12 | 7.1 | 6 | 3.3 | 2 | 1.0 |
| MAGE A4 | 14 | 8.3 | 6 | 3.3 | 3 | 1.6 |
| MMP9 | 17 | 10.1 | 5 | 2.7 | 6 | 3.1 |
| NY-ESO-1 | 21 | 12.4 | 11 | 6.0 | 4 | 2.1 |
| RalA | 12 | 7.1 | 7 | 3.8 | 6 | 3.1 |
| SALL4 | 11 | 6.5 | 7 | 3.8 | 4 | 2.1 |
| Transferrin | 15 | 8.9 | 5 | 2.7 | 10 | 5.2 |
| Panel | 78 | 46.2 | 24 | 87 | 26 | 86.4 |

TABLE 28

| Performance of AAb panel by stage for HCC cohort: number of patients (n) by stage and resultant sensitivity | | | |
|---|---|---|---|
| Stage | n | Positive | Sensitivity (%) |
| BCLC 0 | 1 | 0 | 0.0 |
| BCLC A | 30 | 12 | 40.0 |
| BCLC B | 71 | 32 | 45.1 |
| BCLC C | 28 | 19 | 67.9 |
| BCLC D | 8 | 5 | 62.5 |
| Unknown | 31 | 10 | 32.3 |

BCLC = Barcelona Clinic Liver Cancer (BCLC) staging system

Circulating alpha-fetoprotein (AFP) was measured in the serum samples for the sample set described in Example 6 using a commercially available ELISA (Monobind). A commonly-used cut-off of 200 ng/ml was applied to assess positivity which is broken down by stage in Table 29. AFP antigen sensitivity increases with stage for this cohort, with sensitivity for early stage disease much lower than for late stage disease. It is also worth noting that sensitivity for early stage disease is much lower for AFP antigen compared to the AAb panel for this example, whereas late stage performance is similar.

TABLE 29

Performance of AFP antigen by stage for HCC cohort: number of patients (n) by stage and resultant sensitivity

| Stage | n | Positive | Sensitivity (%) |
|---|---|---|---|
| BCLC 0 | 1 | 0 | 0.0 |
| BCLC A | 30 | 3 | 10.0 |
| BCLC B | 71 | 25 | 35.2 |
| BCLC C | 28 | 16 | 57.1 |
| BCLC D | 8 | 5 | 62.5 |
| Unknown | 31 | 3 | 9.7 |

Positivity and sensitivity for the HCC cohort in Example 6 can be increased by combining the AFP antigen with the AAb panel results (Table 30), improving sensitivity for both early and late stage disease. It is clear from these results that the performance of AFP in combination with the AAb panel is greater than the performance of either AFP or the AAb panel alone (Table 31), Combining the AAb panel with AFP has a minimal effect on specificity.

TABLE 30

Performance of AAb panel + AFP antigen by stage for HCC cohort: number of patients (n) by stage and resultant sensitivity

| Stage | n | Positive | Sensitivity (%) |
|---|---|---|---|
| BCLC 0 | 1 | 0 | 0.0 |
| BCLC A | 30 | 13 | 43.0 |
| BCLC B | 71 | 42 | 59.2 |
| BCLC C | 28 | 25 | 89.3 |
| BCLC D | 8 | 6 | 75.0 |
| Unknown | 31 | 11 | 35.5 |

TABLE 31

Performance of AFP alone and when added to the AAb panel described in Example 6

| Marker combination | Sensitivity | Specificity (Benign) | Specificity (Normal) |
|---|---|---|---|
| AAb panel | 46.2 | 87.0 | 86.4 |
| AFP antigen | 30.8 | 99.5 | 100.0 |
| AAb panel + AFP antigen | 57.4 | 86.4 | 86.4 |

The invention claimed is:

1. A method of detecting and treating liver cancer in a mammalian subject, the method comprising:

(a) obtaining a test sample comprising a bodily fluid from a mammalian subject;

(b) contacting the test sample with a tumour marker antigen panel consisting of MMP9, AIF1, EpCAM and CDKN1B;

(c) detecting the presence or absence of complexes of one or more of the tumour marker antigens, of the tumour marker antigen panel, bound to autoantibodies present in the test sample; and (d) administering a liver cancer treatment to the subject when complexes of the one or more of the tumour marker antigens bound to autoantibodies present in the test sample are detected.

2. The method of claim 1, wherein the mammalian subject has tested positive for alpha-fetoprotein (AFP), des-gamma carboxyprothrombin (DCP) or lectin-reactive alpha-fetoprotein (AFP-L3).

3. The method of claim 1, wherein the mammalian subject has tested positive for liver cancer using ultrasound surveillance.

4. The method of claim 1, wherein the mammalian subject has liver cirrhosis, non-alcoholic fatty liver disease, alcoholic liver disease, Wilson's disease, hereditary hemochromatosis, autoimmune hepatitis, hepatitis B, hepatitis C, documented aflatoxin exposure, schistosomiasis or diabetes mellitus.

5. The method of claim 1, wherein the subject is female.

6. The method of claim 1, wherein the subject is male.

7. The method of claim 1, wherein each of the one or more of the tumour marker antigens is a naturally occurring protein or polypeptide, a recombinant protein or polypeptide, a synthetic protein or polypeptide, a synthetic peptide, a peptide mimetic, a polysaccharide or a nucleic acid.

8. The method of claim 1, wherein the liver cancer is hepatocellular carcinoma (HCC).

9. The method of claim 1, wherein the bodily fluid is chosen from plasma, serum, whole blood, urine, sweat, lymph, faeces, cerebrospinal fluid, ascites fluid, pleural effusion, seminal fluid, sputum, nipple aspirate, post-operative seroma, saliva, amniotic fluid, tears and wound drainage fluid.

10. A method of detecting and treating liver cancer in a mammalian subject, wherein two or more autoantibodies are detected, the method comprising:

(a) obtaining a test sample comprising a bodily fluid from a mammalian subject;

(b) contacting the test sample with a panel of two or more tumour marker antigens comprising a tumour marker antigen panel consisting of MMP9, AIF1, EpCAM and CDKN1B and one or more further tumour marker antigens immunologically specific for at least one of the two or more autoantibodies;

(c) detecting the presence or absence of complexes of the two or more of the tumour marker antigens of the tumour marker antigen panel bound to autoantibodies present in the test sample; and (d) administering a liver cancer treatment to the subject when complexes of the two or more of the tumour marker antigens bound to autoantibodies present in the test sample are detected.

11. The method of claim 10, wherein the two or more tumour marker antigens of the tumour marker antigen panel are distinct antigens.

12. The method of claim 11, wherein the two or more tumour marker antigens of the tumour marker antigen panel comprise two or more antigen variants of one or more of the distinct antigens.

13. The method of claim 10, wherein the one or more further tumour marker antigens are selected from NY-ESO-1, vimentin, HSPA4, transferrin, HNRNP-L, HSPD1, HNRNP-A2, SALL4, Cyclin B1, AFP, NPM1, YWHAZ, DDX3X, p62, CAGE, MAGE A4, RalA, GBU4-5, SOX2, AKR1B10, ApoA1, BCL2, CD44, CK18, CPS1, FUCA1, GLUL, HSPA2, IL-8, MDM2, PEBP1, prolactin, RGN, SPP1, SSX2 and TGFB1.

14. The method of claim 13, wherein the one or more further tumour marker antigens further comprise two or more of the following groups of tumour marker antigens:

(i) CAGE, NY-ESO-1, transferrin, MAGE A4, RalA, HSPA4, SALL4, Cyclin B1, and DDX3X; or (ii) CAGE, NY-ESO-1, transferrin, MAGE A4, RalA, HSPA4, SALL4, Cyclin B1, DDX3X, SOX2 and AFP; or (ii) NY-ESO-1, HSPA4, vimentin, HNRNP-L and transferrin.

15. The method of claim 13, wherein the one or more further tumour marker antigens further comprise at least one of the following groups of tumour marker antigens:

(i) HSPA4 and CPS1; or (ii) CAGE, HSPD1, SOX2, SALL4, HSPA4 and transferrin.

16. The method of claim 13, wherein the one or more further tumour marker antigens further comprise at least one of the following groups of tumour marker antigens:

(i) NY-ESO-1, vimentin, HSPA2, HSPA4 and HNRNP-L; or (ii) CAGE, SOX2, RalA, MAGE A4, DDX3X and NY-ESO-1.

17. The method of claim 13, wherein the one or more further tumour marker antigens further comprise DDX3X, SALL4, MAGE A4, NY-ESO-1, CAGE, RalA and SOX2.

18. The method of claim 13, wherein the method comprises detecting alpha-fetoprotein (AFP), des-gamma carboxyprothrombin (DCP) or lectin-reactive alpha-fetoprotein (AFP-L3) in the test sample comprising a bodily fluid from the mammalian subject.

19. The method of claim 18, wherein the method comprises detecting alpha-fetoprotein (AFP) in the test sample comprising a bodily fluid from the mammalian subject.

20. The method of claim 19, wherein autoantibodies immunologically specific for the tumour marker proteins CAGE, NY-ESO-1, transferrin, MAGE A4, RalA, HSPA4, SALL4, Cyclin B1, and DDX3X are detected in the test sample comprising a bodily fluid from the mammalian subject.

21. The method of claim 19, wherein autoantibodies immunologically specific for the tumour marker proteins CAGE, NY-ESO-1, transferrin, MAGE A4, RalA, HSPA4, SALL4, Cyclin B1, DDX3X, SOX2 and AFP are detected in the test sample comprising a bodily fluid from the mammalian subject.

22. The method of claim 9, wherein the bodily fluid is whole blood.

23. The method of claim 13, wherein the subject is female.

24. The method of claim 13, wherein the subject is male.

25. An in vitro method of determining an antibody profile of an individual suffering from liver cancer in a test sample comprising a bodily fluid from a mammalian subject wherein the antibody is an autoantibody immunologically specific for one or more tumour marker proteins consisting of MMP9, AIF1, EpCAM and CDKN1B, which method comprises the steps of:

(a) contacting the test sample with a tumour marker antigen panel consisting of MMP9, AIF1, EpCAM and CDKN1B; and (b) determining the presence or absence of complexes of one or more of the tumour marker antigens, of the tumour marker antigen panel, bound to autoantibodies present in the test sample, wherein the method is repeated to build up a profile of antibody production.

26. A method of diagnosing and treating liver cancer in a mammalian subject by detecting an antibody in a test sample comprising a bodily fluid from the mammalian subject, wherein the antibody is an autoantibody immunologically specific for one or more tumour marker proteins selected from the group consisting of MMP9, AIF1, EpCAM and CDKN1B, which method comprises the steps of:

(a) contacting the test sample with a tumour marker antigen panel consisting of MMP9, AIF1, EpCAM and CDKN1B;

(b) determining the presence or absence of complexes of one or more of the tumour marker antigens, of the tumour marker antigen panel, bound to autoantibodies present in the test sample;

(c) diagnosing the subject with liver cancer when complexes of the one or more of the tumor marker antigens, of the tumour marker antigen panel, bound to autoantibodies present in the test sample are detected; and (d) administering a liver cancer treatment to the diagnosed subject.

27. A method of predicting response to an anti-liver cancer treatment, the method comprising detecting an antibody in a test sample comprising a bodily fluid from a mammalian subject, wherein the antibody is an autoantibody immunologically specific for one or more tumour marker proteins consisting of MMP9, AIF1, EpCAM and CDKN1B, which method comprises the steps of:

(a) contacting the test sample with a tumour marker antigen panel consisting of MMP9, AIF1, EpCAM and CDKN1B;

(b) determining the presence or absence of complexes of one or more of the tumour marker antigens, of the tumour marker antigen panel, bound to autoantibodies present in the test sample;

(c) detecting an amount of specific binding between the one or more of the tumour marker antigens, of the tumour marker antigen panel, and autoantibodies present in the test sample; and (d) comparing the amount of specific binding between the one or more of the tumour marker antigens, of the tumour marker antigen panel, and the autoantibodies with a previously established relationship between the amount of binding and the likely outcome of treatment; whereby a change in the amount of specific binding, when compared to controls, predicts that the patient will or will not respond to the anti-liver cancer treatment;

(e) administering a liver cancer treatment to the subject when complexes of the one or more of the tumour marker antigens bound to autoantibodies present in the test sample are detected.

28. The method of claim 26, wherein the liver cancer treatment is selected from the group consisting of chemotherapy, radiofrequency ablation, liver resection, liver transplant, vaccination, anti-growth factor or signal transduction therapies, endocrine therapy, human antibody therapy, transcatheter arterial chemoembolization, percutaneous ethanol injection, microwave ablation, sorafenib administration and radioembolisation.

* * * * *